(12) United States Patent
Forton et al.

(10) Patent No.: US 7,985,242 B2
(45) Date of Patent: Jul. 26, 2011

(54) INSTRUMENTS AND METHODS FOR REDUCTION OF VERTEBRAL BODIES

(75) Inventors: Charlie Forton, Leander, TX (US);
Robert J. Jones, Austin, TX (US);
Larry Khoo, Studio City, CA (US);
Michael Landry, Austin, TX (US); Erik Wagner, Austin, TX (US)

(73) Assignee: Zimmer Spine, Inc., Minneapolis, MN (US)

( * ) Notice: Subject to any disclaimer, the term of this patent is extended or adjusted under 35 U.S.C. 154(b) by 1114 days.

(21) Appl. No.: 11/690,698

(22) Filed: Mar. 23, 2007

(65) Prior Publication Data

US 2008/0009864 A1      Jan. 10, 2008

Related U.S. Application Data

(63) Continuation-in-part of application No. 10/980,675, filed on Nov. 3, 2004, now abandoned, and a continuation-in-part of application No. 10/697,793, filed on Oct. 30, 2003, now Pat. No. 7,250,052.

(60) Provisional application No. 60/422,455, filed on Oct. 30, 2002, provisional application No. 60/466,091, filed on Apr. 28, 2003, provisional application No. 60/471,254, filed on May 16, 2003.

(51) Int. Cl.
*A61B 17/58* (2006.01)

(52) U.S. Cl. ........ 606/246; 606/264; 606/265; 606/266; 623/17.11

(58) Field of Classification Search ................... 606/246, 606/250–253, 264–275, 86 R, 99, 86 A
See application file for complete search history.

(56) References Cited

U.S. PATENT DOCUMENTS

| | | | |
|---|---|---|---|
| 5,484,440 | A | 1/1996 | Allard |
| 5,681,319 | A | 10/1997 | Biedermann |
| 5,733,286 | A | 3/1998 | Errico et al. |
| 5,910,141 | A | 6/1999 | Morrison et al. |
| 6,123,707 | A | 9/2000 | Wagner |
| 6,139,549 | A | 10/2000 | Keller |
| 6,183,472 | B1 | 2/2001 | Lutz |
| 6,440,133 | B1 | 8/2002 | Beale |
| 6,458,132 | B2 | 10/2002 | Choi |

(Continued)

FOREIGN PATENT DOCUMENTS

EP    1574175  A1    9/2005

(Continued)

*Primary Examiner* — Thomas C Barrett
*Assistant Examiner* — Michael T Schaper
(74) *Attorney, Agent, or Firm* — Seager, Tufte & Wickhem LLC

(57) ABSTRACT

A spinal stabilization system may be formed in a patient. In some embodiments, a minimally invasive procedure may be used to form a spinal stabilization system in a patient. Bone fastener assemblies may be coupled to vertebrae. Each bone fastener assembly may include a bone fastener and a collar. The collar may be rotated and/or angulated relative to the bone fastener. Extenders may be coupled to the collar to allow for formation of the spinal stabilization system through a small skin incision. The extenders may allow for alignment of the collars to facilitate insertion of an elongated member in the collars. An elongated member may be positioned in the collars and a closure member may be used to secure the elongated member to the collars. A reducer may be used to achieve reduction of one or more vertebral bodies coupled to a spinal stabilization system.

14 Claims, 17 Drawing Sheets

U.S. PATENT DOCUMENTS

| | | | |
|---|---|---|---|
| 6,488,681 B2 | 12/2002 | Martin et al. | |
| 6,530,929 B1 | 3/2003 | Justis et al. | |
| 6,554,834 B1 | 4/2003 | Crozet | |
| 6,648,888 B1 * | 11/2003 | Shluzas | 606/86 A |
| 6,716,214 B1 | 4/2004 | Jackson | |
| 6,743,231 B1 | 6/2004 | Gray et al. | |
| 6,746,449 B2 | 6/2004 | Jones et al. | |
| 6,755,829 B1 | 6/2004 | Bono et al. | |
| 6,790,209 B2 * | 9/2004 | Beale et al. | 606/86 A |
| 6,974,460 B2 | 12/2005 | Carbone et al. | |
| 7,004,947 B2 | 2/2006 | Shluzas et al. | |
| 7,156,849 B2 | 1/2007 | Dunbar et al. | |
| 7,250,052 B2 | 7/2007 | Landry et al. | |
| 7,341,594 B2 | 3/2008 | Shluzas et al. | |
| 7,354,453 B2 | 4/2008 | McAfee | |
| 7,491,218 B2 | 2/2009 | Landry et al. | |
| 7,563,264 B2 | 7/2009 | Landry et al. | |
| 7,569,061 B2 | 8/2009 | Colleran | |
| 7,572,281 B2 | 8/2009 | Runco et al. | |
| 7,604,640 B2 | 10/2009 | Kana | |
| 7,618,444 B2 | 11/2009 | Shluzas | |
| 7,691,132 B2 | 4/2010 | Landry et al. | |
| 7,713,274 B2 | 5/2010 | Shluzas et al. | |
| 2003/0199872 A1 | 10/2003 | Markworth | |
| 2003/0236529 A1 | 12/2003 | Shluzas et al. | |
| 2004/0147937 A1 | 7/2004 | Dunbar et al. | |
| 2005/0125066 A1 | 6/2005 | McAfee | |
| 2005/0245928 A1 | 11/2005 | Colleran et al. | |
| 2005/0273101 A1 | 12/2005 | Schumacher | |
| 2006/0079909 A1 | 4/2006 | Runco et al. | |
| 2006/0095035 A1 | 5/2006 | Jones et al. | |
| 2006/0106394 A1 | 5/2006 | Colleran | |
| 2006/0142761 A1 | 6/2006 | Landry et al. | |
| 2006/0271198 A1 | 11/2006 | McAfee | |
| 2006/0293684 A1 | 12/2006 | Shluzas et al. | |
| 2007/0173745 A1 | 7/2007 | Diederich et al. | |
| 2007/0288026 A1 | 12/2007 | Shluzas | |
| 2007/0299444 A1 | 12/2007 | DiPoto et al. | |
| 2008/0009864 A1 | 1/2008 | Forton et al. | |
| 2008/0015582 A1 | 1/2008 | DiPoto et al. | |
| 2008/0015601 A1 | 1/2008 | Castro et al. | |
| 2008/0033251 A1 | 2/2008 | Araghi | |
| 2008/0039838 A1 | 2/2008 | Landry et al. | |
| 2008/0045957 A1 | 2/2008 | Landry et al. | |
| 2008/0077139 A1 | 3/2008 | Landry et al. | |
| 2008/0077155 A1 | 3/2008 | Diederich et al. | |
| 2008/0177269 A1 | 7/2008 | Seelig | |
| 2008/0183044 A1 | 7/2008 | Colleran et al. | |
| 2008/0183046 A1 | 7/2008 | Boucher et al. | |
| 2008/0188718 A1 | 8/2008 | Spitler et al. | |
| 2008/0200918 A1 | 8/2008 | Spitler et al. | |
| 2008/0200951 A1 | 8/2008 | McAfee | |
| 2008/0221627 A1 | 9/2008 | Shluzas et al. | |
| 2008/0234765 A1 | 9/2008 | Frasier et al. | |
| 2008/0243190 A1 | 10/2008 | Dziedzic et al. | |
| 2008/0300638 A1 | 12/2008 | Beardsley et al. | |
| 2009/0005814 A1 | 1/2009 | Miller et al. | |
| 2009/0030419 A1 | 1/2009 | Runco | |
| 2009/0030420 A1 | 1/2009 | Runco et al. | |
| 2009/0088764 A1 | 4/2009 | Stad | |

FOREIGN PATENT DOCUMENTS

| | | |
|---|---|---|
| EP | 1694226 B1 | 9/2009 |
| WO | 2005055874 A2 | 6/2005 |
| WO | 2005107415 A2 | 11/2005 |
| WO | 2006036224 A2 | 4/2006 |
| WO | 2006036224 A3 | 4/2006 |
| WO | 2006055448 A1 | 5/2006 |
| WO | 2009014856 A2 | 1/2009 |
| WO | 2009042297 A1 | 4/2009 |

* cited by examiner

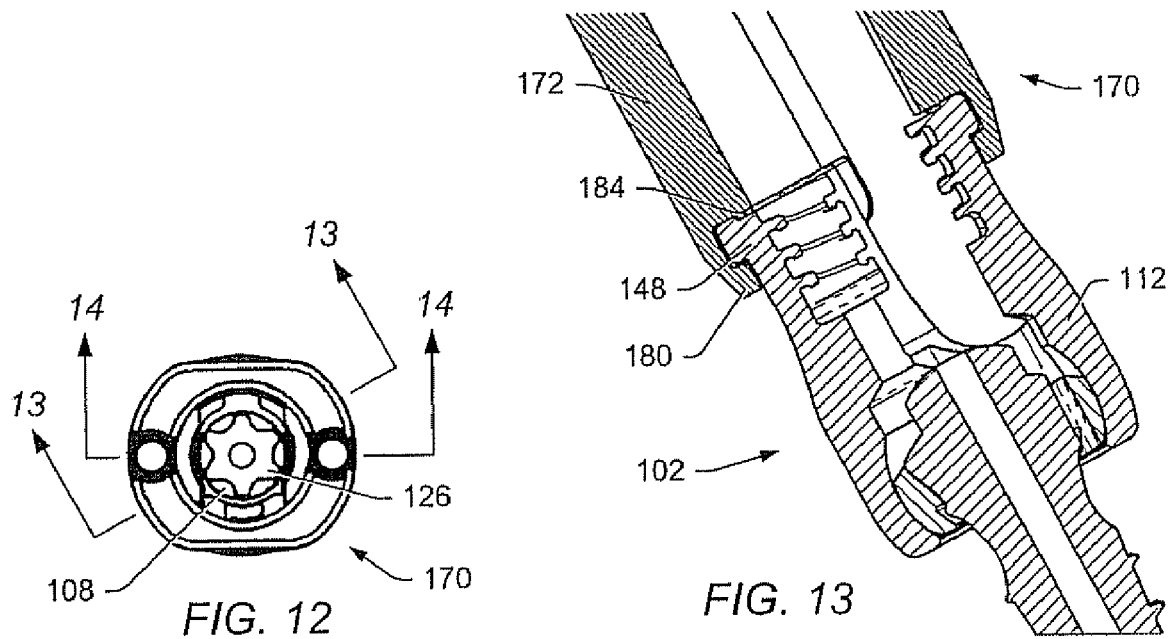
FIG. 12
FIG. 13
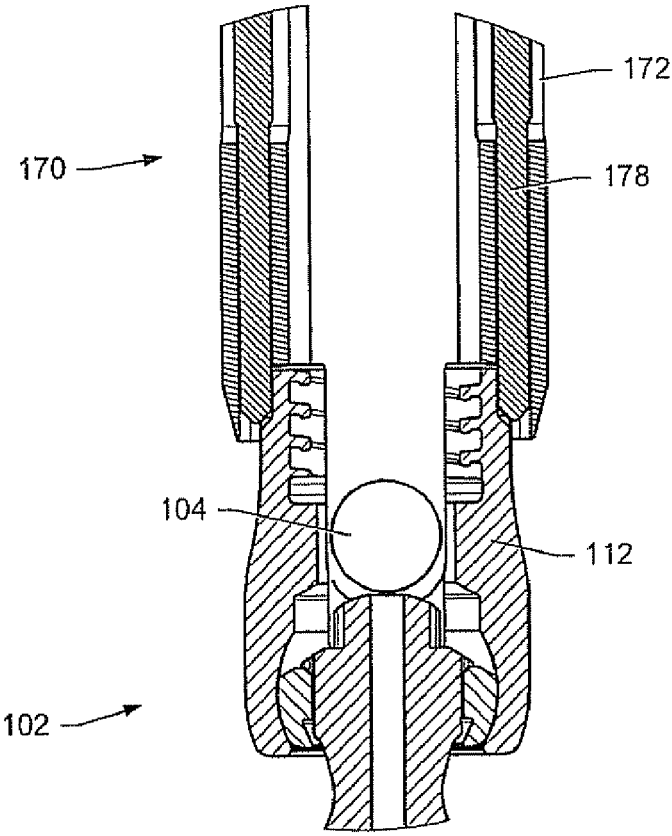
FIG. 14

INSTRUMENTS AND METHODS FOR REDUCTION OF VERTEBRAL BODIES

This application is a continuation-in-part of U.S. patent application Ser. No. 10/980,675, filed Nov. 3, 2004 now abandoned; this application is also a continuation-in-part of U.S. patent application Ser. No. 10/697,793, filed Oct. 30, 2003 now U.S. Pat. No. 7,250,052, which claims priority to U.S. Provisional Application No. 60/422,455, filed Oct. 30, 2002, U.S. Provisional Application No. 60/466,091, filed Apr. 28, 2003, and U.S. Provisional Application No. 60/471,254, filed May 16, 2003; the above-referenced applications are incorporated by reference as if fully set forth herein.

BACKGROUND

1. Field of the Invention

The present invention generally relates to instruments and methods used during a spinal stabilization procedure to join vertebrae together. More particularly, the present invention generally relates to spinal surgical procedure that may use instruments and methods for reducing adjacent vertebrae.

2. Description of Related Art

Bone may be subject to degeneration caused by trauma, disease, and/or aging. Degeneration may destabilize bone and affect surrounding structures. For example, destabilization of a spine may result in alteration of a natural spacing between adjacent vertebrae. Alteration of a natural spacing between adjacent vertebrae may subject nerves that pass between vertebral bodies to pressure. Pressure applied to the nerves may cause pain and/or nerve damage. Maintaining the natural spacing between vertebrae may reduce pressure applied to nerves that pass between vertebral bodies. A spinal stabilization procedure may be used to maintain the natural spacing between vertebrae and promote spinal stability.

Spinal stabilization may involve accessing a portion of the spine through soft tissue. Conventional stabilization systems may require a large incision and/or multiple incisions in the soft tissue to provide access to a portion of the spine to be stabilized. Conventional procedures may result in trauma to the soft tissue, for example, due to muscle stripping.

Spinal stabilization systems for a lumbar region of the spine may be inserted during a spinal stabilization procedure using a posterior spinal approach. Conventional systems and methods for posterolateral spinal fusion may involve dissecting and retracting soft tissue proximate the surgical site. Dissection and retraction of soft tissue may cause trauma to the soft tissue, and extend recovery time. Minimally invasive procedures and systems may reduce recovery time as well as trauma to the soft tissue surrounding a stabilization site.

U.S. Pat. No. 6,530,929 to Justis et al. hereinafter "Justis"), which is incorporated by reference as if fully disclosed herein, describes minimally invasive techniques and instruments for stabilizing a bony structure in an animal subject. Justis provides a method for using an instrument to connect at least two bone anchors with a connecting element. The instrument is secured to the anchors and manipulated to place the connecting element in a position more proximate the anchors. The Justis system is a constrained system. An elongated member installed using the Justis instruments and method must have a set curvature to function with the installation instruments.

U.S. Patent Publication No. U.S. 2004 0138662 to Landry et al. (hereinafter "Landry"), which is incorporated by reference as if fully disclosed herein, describes a minimally invasive procedure and instruments for stabilizing a portion of the spine. The Landry system is not a constrained system. An elongated member installed using the Landry instruments and method does not need to have a curvature defined by the insertion instruments.

SUMMARY

A spinal stabilization system may be installed in a patient to stabilize a portion of a spine. A spinal stabilization system may be installed using a minimally invasive procedure. An instrumentation kit may provide instruments and spinal stabilization system components necessary for forming a spinal stabilization system in a patient. The instrumentation kit may include a reducer. The reducer may be used with a spinal stabilization system formed in the patient. The reducer may change the distance in the anterio-posterior plane between adjacent vertebrae. The reducer may seat an elongated member of a spinal stabilization system in a collar of a bone fastener assembly that is coupled to a vertebra.

A spinal stabilization system may be used to achieve rigid pedicle fixation while minimizing the amount of damage to surrounding tissue. In some embodiments, a spinal stabilization system may be used to provide stability to two or more vertebrae. A spinal stabilization system may include an elongated member, two or more bone fastener assemblies, and/or closure members.

A bone fastener assembly may include, but is not limited to, a bone fastener and a collar. A first portion of the bone fastener may couple to a vertebra. A first portion of a collar may couple to a second portion of the bone fastener. A second portion of the collar may couple to an elongated member during use. In some embodiments, an orientation of the bone fastener may be independent of the orientation of the collar. After the bone fastener is placed in a vertebral body, the collar coupled to the bone fastener may be positioned so that the elongated member can be positioned in the collar and in at least one other collar that is coupled to another vertebral body by a bone fastener.

In some embodiments, when an elongated member is coupled to a first bone fastener assembly, the elongated member may not be seated in a collar of a second bone fastener assembly. A reducer may be used to seat the elongated member in the collar of the second bone fastener assembly. During an invasive surgical procedure, access to the collar of the second bone fastener and the elongated member may be sufficient to allow a reducer to be attached to the collar and to the elongated member to achieve reduction using the reducer. During a minimally invasive surgical procedure, direct access to the collar and the elongated member may not be possible. In some embodiments, a reducer may couple to an extender coupled to the collar and to the elongated member. In some embodiments, a reducer may couple to the extender coupled to the collar and to a sleeve coupled to the elongated member.

To achieve reduction of a first vertebra relative to a second vertebra, a first bone fastener assembly may be secured to a first vertebra. A second bone fastener assembly may be secured to a second vertebra. An elongated member may be positioned in a collar of the first bone fastener assembly. A closure member may be secured to the collar of the first bone fastener assembly to secure the position of the elongated member relative to the first vertebra and the first bone fastener assembly. A portion of the elongated member may extend to the second collar. A reducer may be coupled to the collar of the second bone fastener assembly and the elongated member. The reducer may be used to seat the elongated member in the collar of the second bone fastener assembly. When the reducer seats the elongated member in the collar of the second bone fastener assembly, a closure member may be secured to the collar to fix the position of the elongated member relative to the second bone fastener assembly.

After the elongated member has been seated and secured in collars of bone fastener assemblies, imaging techniques may be used to confirm the position of the installed spinal stabilization system. When the spinal stabilization system is positioned as desired, a driver may be used to shear off tool portions of closure members. A counter torque wrench may be used to counteract force applied to the spinal stabilization system so that the force applied to shear the tool portion of a closure member is not transmitted to the patient.

BRIEF DESCRIPTION OF THE DRAWINGS

Advantages of the present invention will become apparent to those skilled in the art with the benefit of the following detailed description and upon reference to the accompanying drawings in which:

FIG. 12 depicts a top view of an embodiment of a multi-channel extender with a bone fastener assembly coupled to the extender.

FIG. 13 depicts a cross-sectional representation of a portion of the extender with the bone fastener assembly taken substantially along line 13-13 of FIG. 12.

FIG. 14 depicts a cross-sectional representation of a portion of the extender with the bone fastener assembly taken substantially along line 14-14 of FIG. 12.

Figure 1:
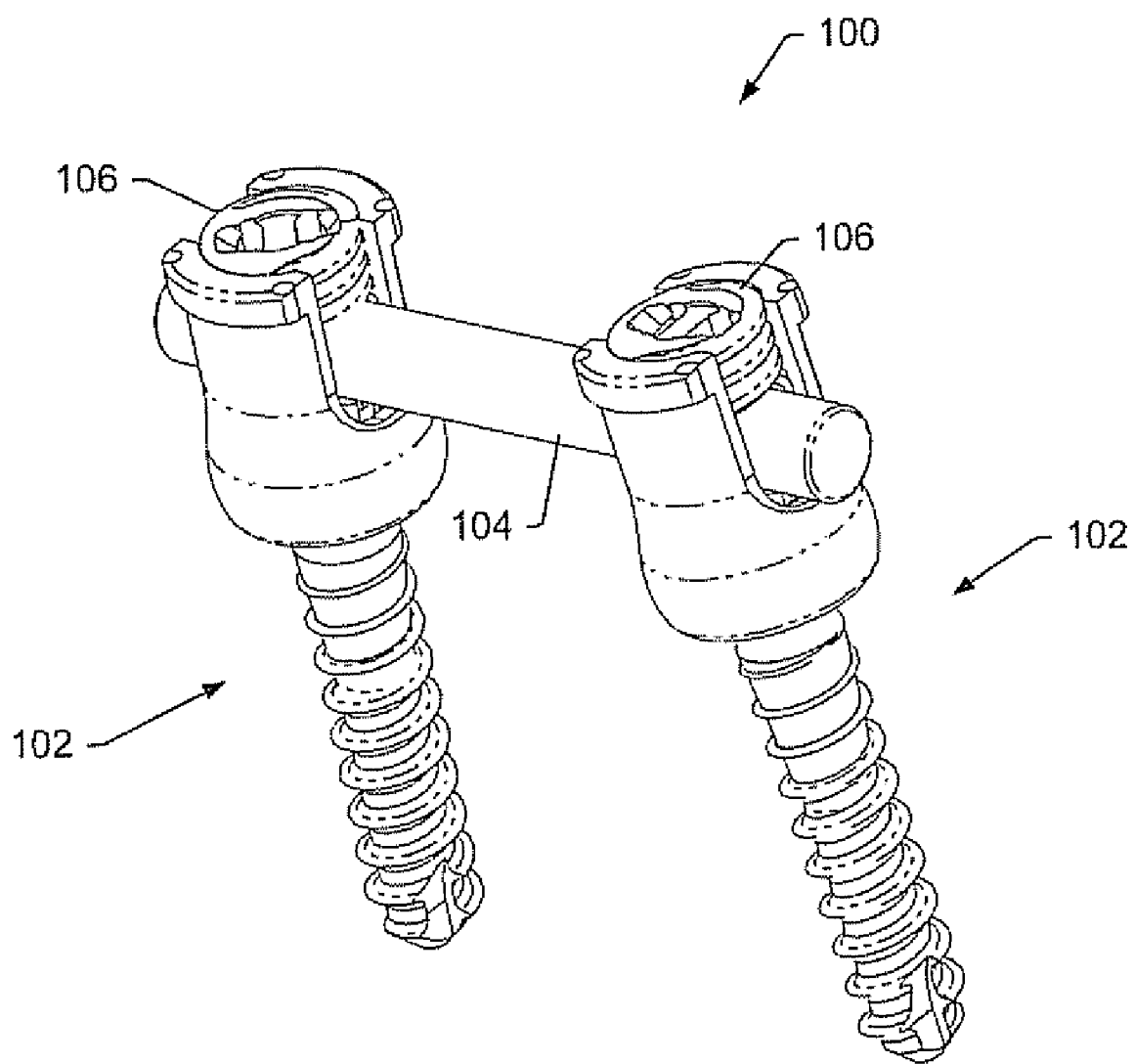
FIG. 1 depicts a perspective view of an embodiment of a spinal stabilization system.

While the invention is susceptible to various modifications and alternative forms, specific embodiments thereof are shown by way of example in the drawings and will herein be described in detail. The drawings may not be to scale. It should be understood that the drawings and detailed description thereto are not intended to limit the invention to the particular form disclosed, but on the contrary, the intention is to cover all modifications, equivalents, and alternatives falling within the spirit and scope of the present invention as defined by the appended claims.

DETAILED DESCRIPTION

A spinal stabilization system may be installed in a patient to stabilize a portion of a spine. Spinal stabilization may be used, but is not limited to use, in patients having degenerative disc disease, spinal stenosis, spondylolisthesis, pseudoarthrosis, and/or spinal deformities; in patients having fracture or other vertebral trauma; and in patients after tumor resection. A spinal stabilization system may be installed using a minimally invasive procedure. An instrumentation set may include instruments and spinal stabilization system components for forming a spinal stabilization system in a patient and for facilitating reduction of one or more vertebral bodies.

A minimally invasive procedure may be used to limit an amount of trauma to soft tissue surrounding vertebrae that are to be stabilized. In some embodiments, the natural flexibility of skin and soft tissue may be used to limit the length and/or depth of an incision or incisions needed during the stabilization procedure. Minimally invasive procedures may provide limited direct visibility in vivo. Forming a spinal stabilization system using a minimally invasive procedure may include using tools to position system components in the body.

A minimally invasive procedure may be performed after installation of one or more spinal implants in a patient. The spinal implant or spinal implants may be inserted using an anterior procedure and/or a lateral procedure. The patient may be turned and a minimally invasive procedure may be used to install a posterior spinal stabilization system. A minimally invasive procedure for stabilizing the spine may be performed without prior insertion of one or more spinal implants in some patients. In some patients, a minimally invasive procedure may be used to install a spinal stabilization system after one or more spinal implants are inserted using a posterior spinal approach.

A spinal stabilization system may be used to achieve rigid pedicle fixation while minimizing the amount of damage to surrounding tissue. In some embodiments, a spinal stabilization system may be used to provide stability to two adjacent vertebrae (i.e., one vertebral level). A spinal stabilization system may include two bone fastener assemblies. One bone fastener assembly may be positioned in each of the vertebrae to be stabilized. An elongated member may be coupled and secured to the bone fastener assemblies. As used herein, "coupled" components may directly contact each other or may be separated by one or more intervening members. In some embodiments, a single spinal stabilization system may be installed in a patient. Such a system may be referred to as a unilateral, single-level stabilization system or a single-level, two-point stabilization system. In some embodiments, two spinal stabilization systems may be installed in a patient on opposite sides of a spine. Such a system may be referred to as a bilateral, single-level stabilization system or a single-level, four-point stabilization system.

In some embodiments, a spinal stabilization system may provide stability to three or more vertebrae (i.e., two or more vertebral levels). In a two vertebral level spinal stabilization system, the spinal stabilization system may include three bone fastener assemblies. One bone fastener assembly may be positioned in each of the vertebrae to be stabilized. An elongated member may be coupled and secured to the three bone fastener assemblies. In some embodiments, a single two-level spinal stabilization system may be installed in a patient. Such a system may be referred to as a unilateral, two-level stabilization system or a two-level, three-point stabilization system. In some embodiments, two three-point spinal stabilization systems may be installed in a patient on opposite sides of a spine. Such a system may be referred to as a bilateral, two-level stabilization system or a two-level, six-point stabilization system.

In some embodiments, combination systems may be installed. For example, a two-point stabilization system may be installed on one side of a spine, and a three-point stabilization system may be installed on the opposite side of the spine. The composite system may be referred to a five-point stabilization system.

Minimally invasive procedures may reduce trauma to soft tissue surrounding vertebrae that are to be stabilized. Only a small opening may need to be made in a patient. For example, for a single-level stabilization procedure on one side of the spine, the surgical procedure may be performed through a 2 cm to 4 cm incision formed in the skin of the patient. In some embodiments, the incision may be above and between the vertebrae to be stabilized. Dilators, a targeting needle, and/or a tissue wedge may be used to provide access to the vertebrae to be stabilized without the need to form an incision with a scalpel through muscle and other tissue between the vertebrae to be stabilized. A minimally invasive procedure may reduce an amount of postoperative pain felt by a patient as compared to invasive spinal stabilization procedures. A minimally invasive procedure may reduce recovery time for the patient as compared to invasive spinal procedures.

Components of spinal stabilization systems may be made of materials including, but not limited to, titanium, titanium alloys, stainless steel, ceramics, and/or polymers. Some components of a spinal stabilization system may be autoclaved and/or chemically sterilized. Components that may not be autoclaved and/or chemically sterilized may be made of sterile materials. Components made of sterile materials may be placed in working relation to other sterile components during assembly of a spinal stabilization system.

Spinal stabilization systems may be used to correct problems in lumbar, thoracic, and/or cervical portions of a spine. Various embodiments of a spinal stabilization system may be used from the C1 vertebra to the sacrum. For example, a spinal stabilization system may be implanted posterior to the spine to maintain distraction between adjacent vertebral bodies in a lumbar portion of the spine.

FIG. 1 depicts an embodiment of spinal stabilization system 100 that may be implanted using a minimally invasive surgical procedure. Spinal stabilization system 100 may include bone fastener assemblies 102, elongated member 104, and/or closure members 106. Other spinal stabilization system embodiments may include, but are not limited to, plates, dumbbell-shaped members, and/or transverse connectors. FIG. 1 depicts a spinal stabilization system for one vertebral level. In some embodiments, the spinal stabilization system of FIG. 1 may be used as a multi-level spinal stabilization system if one or more vertebrae are located between the vertebrae in which bone fastener assemblies 102 are placed. In other embodiments, multi-level spinal stabilization systems may include additional bone fastener assemblies to couple to one or more other vertebrae.

Figure 2:
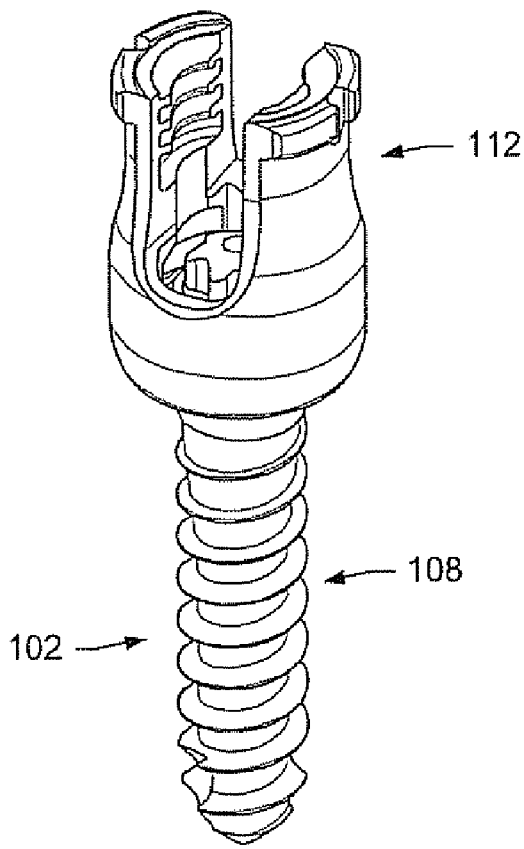
FIG. 2 depicts a perspective view of an embodiment of a bone fastener assembly.
Figure 3:
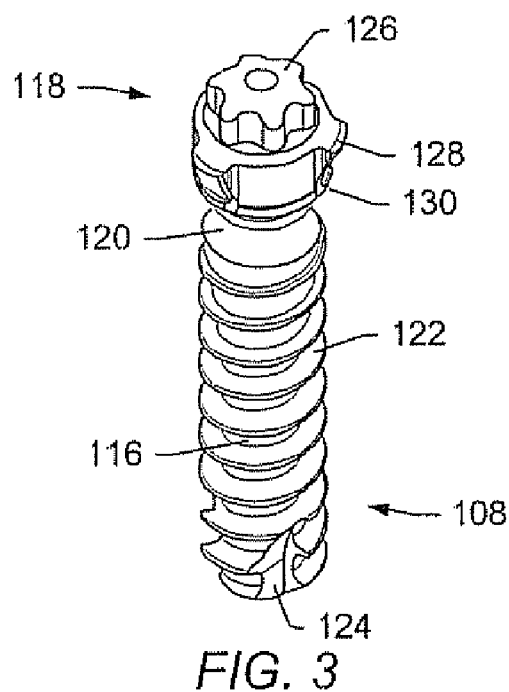
FIG. 3 depicts a perspective view of an embodiment of a bone fastener.
Figure 4:
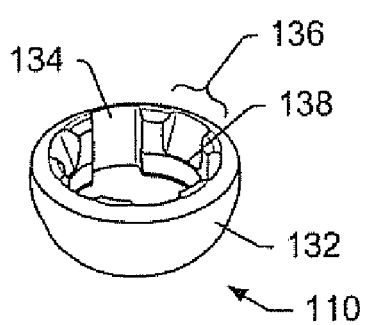
FIG. 4 depicts a perspective view of an embodiment of a bone fastener assembly ring.
Figure 5:
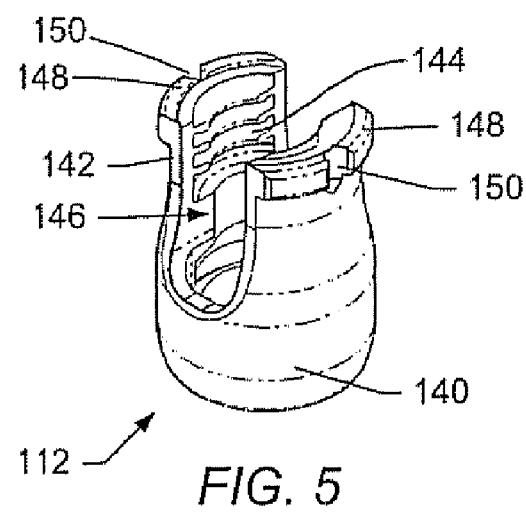
FIG. 5 depicts a perspective view of an embodiment of a bone fastener assembly collar.

FIG. 2 depicts a perspective view of bone fastener assembly 102. FIGS. 3-5 depict embodiments of bone fastener assembly components. Components of bone fastener assembly 102 may include, but are not limited to, bone fastener 108 (shown in FIG. 3), ring 110 (shown in FIG. 4), and collar 112 (shown in FIG. 5). Bone fastener 108 may couple bone fastener assembly 102 to a vertebra. Ring 110 may be positioned between a head of bone fastener 108 and collar 112.

Figure 6:
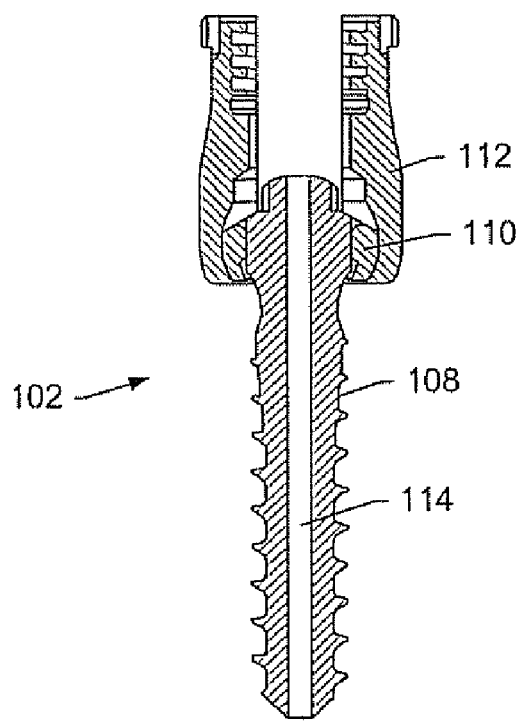
FIG. 6 depicts a cross-sectional view of an embodiment of a bone fastener assembly.

FIG. 6 depicts a cross-sectional representation of bone fastener 108, ring 110, and collar 112 of bone fastener assembly 102. Bone fastener 108 of bone fastener assembly 102 may include passage 114. A guide wire may be placed through passage 114 so that bone fastener 108 may be inserted into a vertebra at a desired location and in a desired angular orientation relative to the vertebra with limited or no visibility of the vertebra.

A bone fastener may be, but is not limited to, a bone screw, a ring shank fastener, a barb, a nail, a brad, or a trocar. Bone fasteners and/or bone fastener assemblies may be provided in various lengths in an instrumentation set to accommodate variability in vertebral bodies. For example, an instrumentation set for stabilizing vertebrae in a lumbar region of the spine may include bone fastener assemblies with lengths ranging from about 30 mm to about 75 mm in 5 mm increments.

FIG. 3 depicts an embodiment of bone fastener 108. Bone fastener 108 may include shank 116, head 118, and neck 120. Shank 116 may include threading 122. In some embodiments, threading 122 may include self-tapping start 124. Self-tapping start 124 may facilitate insertion of bone fastener 108 into vertebral bone.

Head 118 of bone fastener 108 may include various configurations to engage a driver that inserts the bone fastener into a vertebra. In some embodiments, the driver may also be used to remove an installed bone fastener from a vertebra. In some embodiments, head 118 may include one or more tool portions 126. Tool portions 126 may be recesses and/or protrusions designed to engage a portion of the driver.

Head 118 of bone fastener 108 may include one or more splines 128, as depicted in FIG. 3. In some head embodiments, head 118 may include three splines. Splines 128 may be equally spaced circumferentially around head 118 of bone fastener 108. In some head embodiments, splines 128 may be spaced at unequal distances circumferentially around head 118. Splines 128 may include various surface configurations and/or texturing to enhance coupling of bone fastener 108 with a ring of a bone fastener assembly. In some embodiments, sides of the splines may be tapered so that the splines form a dovetail connection with a ring. In some embodiments, spline width may be tapered so that a good interference connection is established when the bone screw is coupled to a ring. Splines 128 may include one or more projections 130 to facilitate coupling bone fastener 108 with an inner surface of a ring. In some embodiments, projections 130 may be positioned on a lower portion of splines 128. In some embodiments, the splines may include recessed surfaces that accept projections extending from surfaces of the ring.

Neck 120 of bone fastener 108 may have a smaller diameter than adjacent portions of head 118 and shank 116. The diameter of neck 120 may fix the maximum angle that the collar of the bone fastener assembly can be rotated relative to bone fastener 108. In some embodiments, neck 120 may be sized to allow up to about 40° or more of angulation of the collar relative to the bone fastener. In some embodiments, the neck may be sized to allow up to about 30° of angulation of the collar relative to the bone fastener. In some embodiments, the neck may be sized to allow up to about 20° of angulation of the collar relative to the bone fastener.

FIG. 4 depicts a perspective view of an embodiment of ring 110. Outer surface 132 of ring 110 may have a contour that substantially complements a contour of an inner surface of a collar in which the ring resides. A contour of the outer surface of the ring may be a spherical portion. When the ring is positioned in the collar, the complementary shape of the ring outer surface and the inner surface of the collar that contacts the ring allows angulation of the collar relative to a bone fastener coupled to the ring. The contour of the outer surface of the ring and the inner surface of the collar may inhibit removal of the ring from the collar after insertion of the ring into the collar.

Outer surface 132 of ring 110 may have a smooth finish. In some embodiments, outer surface 132 may be surface treated or include coatings and/or coverings. Surface treatments, coatings, and/or coverings may be used to adjust frictional and/or wear properties of the outer surface of the ring.

An inner surface of ring 110 may include one or more grooves 134 and/or one or more seats 136. Seats 136 may be circumferentially offset from grooves 134. Grooves 134 may be sized to allow passage of splines of a bone fastener (e.g., splines 128 shown in FIG. 3) through the ring. When the splines are inserted through grooves 134, the bone fastener may be rotated until the splines align with seats 136. The bone fastener may be pulled or driven so that the splines are positioned in seats 136. In some embodiments, projections (e.g., projections 130 in FIG. 3) may pass over ridges 138 of ring 110. Passage of the projections over ridges 138 may securely couple the bone fastener to the ring and inhibit separation of the ring from the bone fastener.

As used herein, the term "collar" includes any element that wholly or partially encloses or receives one or more other elements. A collar may enclose or receive elements including, but not limited to, a bone fastener, a closure member, a ring, and/or an elongated member. In some embodiments, a collar may couple two or more other elements together (e.g., an elongated member and a bone fastener). In some embodiments, a collar may have a "U" shape, however it is to be understood that a collar may also have other shapes.

Collar 112 may include body 140 and arms 142. Arms 142 may extend from body 140. Body 140 of collar 112 may be greater in width than a width across arms 142 of collar 112 (i.e., body 140 may have a maximum effective outer diameter greater than a maximum effective outer diameter of arms 142). A reduced width across arms 142 may allow an extender to be coupled to the arms without substantially increasing a maximum effective outer diameter along a length of collar 112. Thus, a reduced width across arms 142 may reduce bulk at a surgical site.

Inner surfaces of arms 142 may include the reading 144. Threading 144 may engage complementary threading of a closure member to secure an elongated member to a bone fastener assembly.

Arms 142 and body 140 may form slot 146. Slot 146 may be sized to receive an elongated member. When an elongated member is positioned in slot 146, a portion of the elongated member may contact a head of a bone fastener positioned in the collar.

Arms 142 may include ridges or flanges 148. Flange 148 may allow collar 112 to be coupled to an extender so that translational motion of the collar relative to the extender is inhibited. Flanges 148 may also include notches 150. A movable member of an extender may extend into notch 150. When the movable member is positioned in notch 150, a channel in the extender may align with a slot in collar 112. With the movable member positioned in notch 150, rotational movement of collar 112 relative to the extender may be inhibited.

Figure 7:
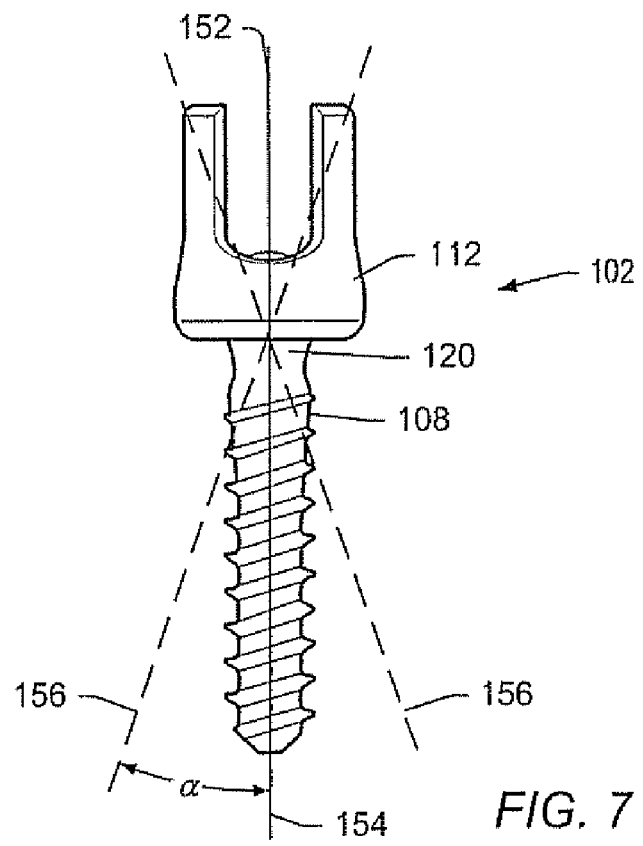
FIG. 7 depicts a front view of an embodiment of a bone fastener assembly with a collar that allows for angulation of a bone fastener relative to the collar in a conical range of motion that is symmetrical relative to an axis that passes through a central axis of the collar and a central axis of a bone fastener.

A bone fastener may be positioned in a collar such that the bone fastener is able to move radially and/or rotationally relative to the collar (or the collar relative to the bone fastener) within a defined range of motion. Motion of the bone fastener relative to the collar (or the collar relative to the bone fastener) may be referred to as "angulation" and/or "polyaxial movement". FIG. 7 depicts bone fastener assembly 102 with central axis 152 of collar 112 aligned with central axis 154 of bone fastener 108. Bone fastener 108 may be angulated in a symmetrical conical range of motion characterized by angle α about the aligned axes. Bone fastener 108 may be constrained from motion outside of limit axis 156 by contact between neck 120 of bone fastener 108 and collar 112. Alignment of axis 154 of bone fastener 108 with central axis 152 of collar 112 may be considered a neutral position relative to the range of motion. The alignment is a neutral position because bone fastener 108 may be angulated an equal amount in any direction from central axis 152. When a driver is inserted into bone fastener 108, axis 154 of bone fastener 108 may be substantially aligned with axis 152 of collar 112 to facilitate insertion of the bone fastener into a vertebral body.

Figure 8:
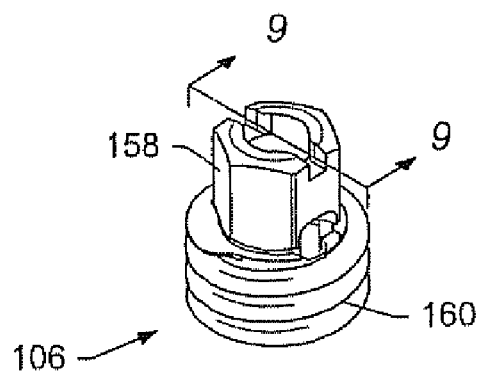
FIG. 8 depicts a perspective view of an embodiment of a closure member.

A closure member may be coupled to a collar of a bone fastener assembly to fix an elongated member positioned in the collar to the bone fastener assembly. FIG. 1 depicts closure members 106 coupled to bone fastener assemblies 102. FIG. 8 depicts closure member 106 prior to insertion of the closure member into a collar of a bone fastener assembly. Closure member 106 may include tool portion 158 and male threading 160. Tool portion 158 may couple to a tool that allows closure member 106 to be positioned in a collar. Tool portion 158 may include various configurations (e.g., threads, hexalobular connections, hexes) for engaging a tool (e.g., a driver). Male threading 160 may have a shape that complements the shape of female threading in arms of a collar (e.g., threading 144 depicted in FIG. 5).

Figure 9:
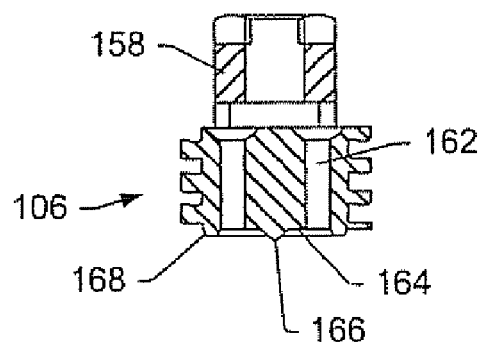
FIG. 9 depicts a cross-sectional representation of the closure member taken substantially along plane 9-9 indicated in FIG. 8.

FIG. 9 depicts a cross-sectional representation of closure member 106 taken substantially along plane 9-9 of FIG. 8. Closure member 106 may include removal openings 162. A drive tool may be inserted into removal openings 162 to allow removal of closure member 106 after tool portion 158 has been sheared off. Removal openings 162 may include any of a variety of features including, but not limited to, sockets, holes, slots, and/or combinations thereof. In an embodiment, removal openings 162 are holes that pass through bottom surface 164 of closure member 106.

A bottom surface of a closure member may include structure and/or texturing that promotes contact between the closure member and an elongated member. A portion of the structure and/or texturing may enter and/or deform an elongated member when the closure member is coupled to the elongated member. Having a portion of the closure member enter and/or deform the elongated member may couple the elongated member to the closure member and a bone fastener assembly so that movement of the elongated member relative to the bone fastener assembly is inhibited. In a closure member embodiment, such as the embodiment depicted in FIG. 9, bottom surface 164 of closure member 106 may include point 166 and rim 168. In some embodiments, rim 168 may come to a sharp point. In some embodiments, a height of rim 168 may be less than a height of point 166. In other embodiments, a height of rim 168 may be the same or larger than a height of point 166. In some embodiments, rim 168 may not extend completely around the closure member. For example, eight or more portions of rim 168 may be equally spaced circumferentially around closure member 106. In certain embodiments, a solid central core including point 166 and rim 168 may enhance the ability of closure member 106 to secure an elongated member in a collar.

Figure 10:
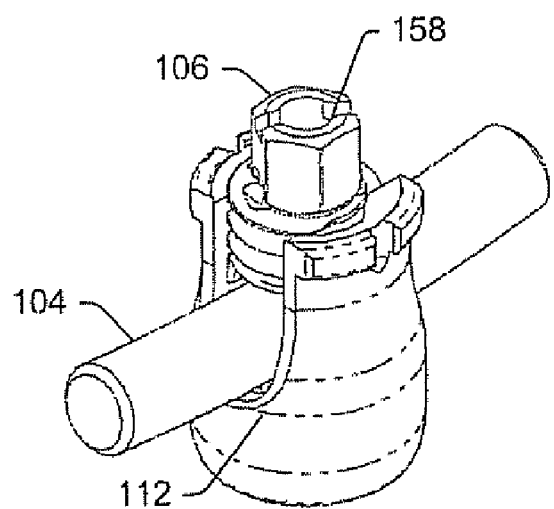
FIG. 10 depicts a perspective view of an embodiment of a portion of a spinal stabilization system.

FIG. 10 depicts a portion of a spinal stabilization system with closure member 106 coupled to collar 112 before tool portion 158 is sheared off. Closure member 106 may couple to collar 112 by a variety of systems including, but not limited to, standard threads, modified threads, reverse angle threads, buttress threads, or helical flanges. Closure member 106 may be advanced into an opening in a collar to engage a portion of elongated member 104. In some embodiments, closure member 106 may inhibit movement of elongated member 104 relative to collar 112.

Various instruments may be used in a minimally invasive procedure to form a spinal stabilization system in a patient. The instruments may include, but are not limited to, positioning needles, guide wires, dilators, bone awls, bone taps, sleeves, extenders, drivers, tissue wedges, elongated member length estimating tools, mallets, tissue retractors, and tissue dilators. The instruments may be provided in an instrumentation set. The instrumentation set may also include components of the spinal stabilization system. The components of the spinal stabilization system may include, but are not limited to, bone fastener assemblies of various sizes and/or lengths, elongated members, and closure members.

Instruments used to install a spinal stabilization system may be made of materials including, but not limited to, stainless steel, titanium, titanium alloys, ceramics, and/or polymers. Some instruments may be autoclaved and/or chemically sterilized. Some instruments may be, or may include, components that cannot be autoclaved or chemically sterilized. Instruments or components of instruments that cannot be autoclaved or chemically sterilized may be made of sterile materials.

An extender may be used as a guide to install bone fasteners of a bone fastener assembly in vertebral bone. An extender may be coupled to a collar of a bone fastener assembly. A distal end of an extender may be tapered or angled to reduce bulk at a surgical site. Instruments may be inserted into the extender to manipulate the bone fastener assembly. Movement of the extender may alter an orientation of a collar relative to a bone fastener of the bone fastener assembly. In some embodiments, an extender may be used as a retractor during a spinal stabilization procedure.

An extender for a single-level vertebral stabilization system may include one or more channels in a wall of the extender to allow access to an adjacent vertebra. For some single-level vertebral stabilization procedures, only single-channel extenders (i.e., extenders with a single channel in a wall of the extender) may be used. For other single-level vertebral stabilization procedures, one or more multi-channel extenders (i.e., extenders with two or more channels in a wall of the extender) may be used. Channels may provide flexibility to or enhance flexibility of a multi-channel extender. In some embodiments, a proximal portion of a multi-channel extender may have a solid circumference. A region of solid circumference in a multi-channel extender may enhance stability of the multi-channel extender. In some embodiments, a multi-channel extender may be longer than a single-channel extender.

An extender used at a middle vertebra in a multi-level stabilization procedure may be a multi-channel extender. Channels in a multi-channel extender may allow access to adjacent vertebrae from a middle vertebra. An extender used at an end vertebra of a multi-level stabilization system may be a single-channel extender or a multi-channel extender. A system for coupling a bone fastener assembly to a multi-channel extender may include a limiter that inhibits spreading of arms of the extender to inhibit release of the bone fastener assembly from the extender.

Instruments may access a bone fastener assembly through a passage in an extender. In some embodiments, a channel in a wall of an extender may extend a full length of the extender. In some embodiments, especially in embodiments of multi-channel extenders, a channel in a wall of an extender may extend only a portion of the length of the extender. A channel may extend to a distal end of an extender such that an elongated member inserted in the channel may pass from the extender into a slot of a collar of a bone fastener assembly coupled to the extender.

A channel in an extender may be any of a variety of shapes. A channel may have a width that exceeds a width (e.g., a diameter) of an elongated member that is to be inserted in the channel. In some embodiments, a channel may be a linear opening parallel to a longitudinal axis of the extender.

Movable members may extend through portions of an extender proximate a channel in the extender. Movable members may engage notches in a collar to establish a radial orientation of the extender on the collar and/or to inhibit rotation of the collar relative to the extender. In some embodiments, a distal end of a movable member may be a projection that engages an opening in a collar. In certain embodiments, a proximal end of a movable member may include a tool portion. The tool portion may facilitate engaging the collar with the extender.

Figure 11:
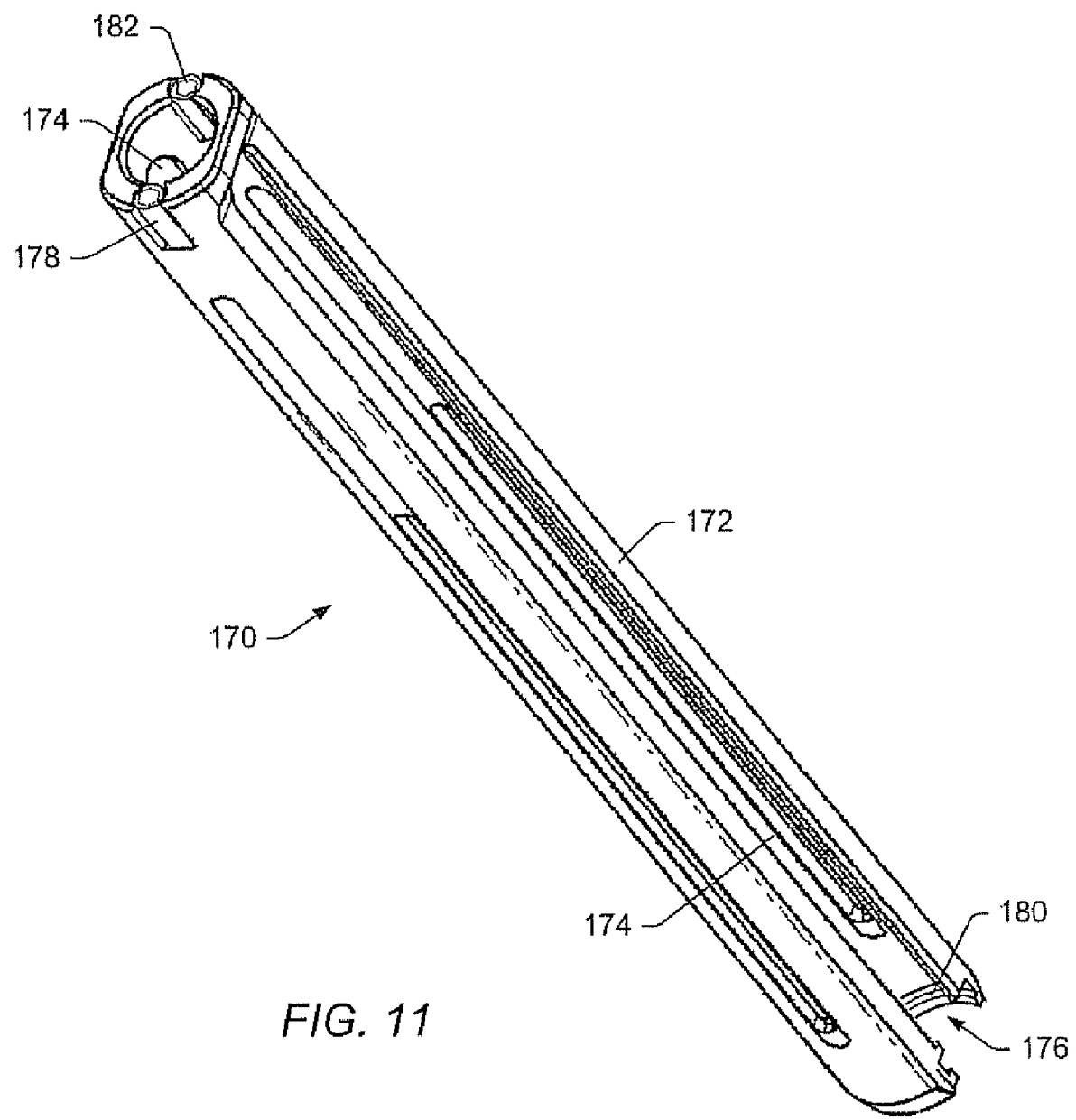
FIG. 11 depicts a perspective view of an embodiment of a multi-channel extender.

FIG. 11 depicts an embodiment of extender 170. Extender 170 may be a multi-channel extender. Extender 170 may include wall 172, channels 174, passage 176, movable members 178, and flange 180. Channels 174 may extend from a distal end of extender 170 through a portion of wall 172. Channels 174 may allow instruments to be positioned and used to form a plane through soft tissue to one or more adjacent vertebrae. An elongated member may be inserted in the tissue plane and positioned in collars of bone fastener assemblies anchored in vertebrae and coupled to extenders. Passage 176 may allow instruments to be positioned and used to manipulate a bone fastener assembly that is coupled to a distal end of extender 170. Movable members 178 may be part of a system that couples a bone fastener assembly to extender 170. In some embodiments, movable members 178 may include tool portion 182. A driver may be positioned in tool portion 182. The driver (e.g., a hex wrench) may be used to extend or retract a distal end of movable member 178. A distal end of extender 170 may include flange 180 that mates with a complementary flange on a collar of a bone fastener assembly. A distal end of extender 170 may be tapered to reduce bulk (e.g., reduce spin diameter) at a surgical site.

FIG. 12 depicts a top view of an embodiment of extender 170 coupled to a bone fastener assembly. Tool portion 126 of bone fastener 108 is a hexalobular connection.

FIG. 13 depicts a cross-sectional representation of a portion of extender 170 with bone fastener assembly 102 taken substantially along line 13-13 of FIG. 12. Flange 180 of extender 170 may mate with flange 148 of collar 112 to inhibit translation of the extender relative to the collar. Extender 170 may also include stop 184. Stop 184 may engage a portion of collar 112 to inhibit separation of walls 172. During use, stop 184 may inhibit undesired separation of bone fastener assembly 102 from extender 170.

FIG. 14 depicts a cross-sectional representation of a portion of extender 170 with bone fastener assembly 102 and elongated member 104 taken substantially along line 14-14 of FIG. 12. Distal ends of movable members 178 may extend into notches (e.g., notches 150 depicted in FIG. 5) in collar 112. Portions of walls 172 of extender 170 may include threading. Portions of movable members 178 may include threading complementary to threaded portions of walls 172. Threading of movable members 178 may engage threading in walls 172 such that rotation of the movable members advances or retracts the movable members relative to the walls.

As shown in FIG. 14, collar 112 may be designed such that elongated member 104 lies below a distal end of extender 170. Coupling extender 170 to collar 112 above elongated member 104 may reduce bulk at a surgical site. With elongated member 104 coupled to collar 112 below a distal end of extender 170, the extender may be removed without interference from the elongated member of a spinal stabilization system.

Figure 15:
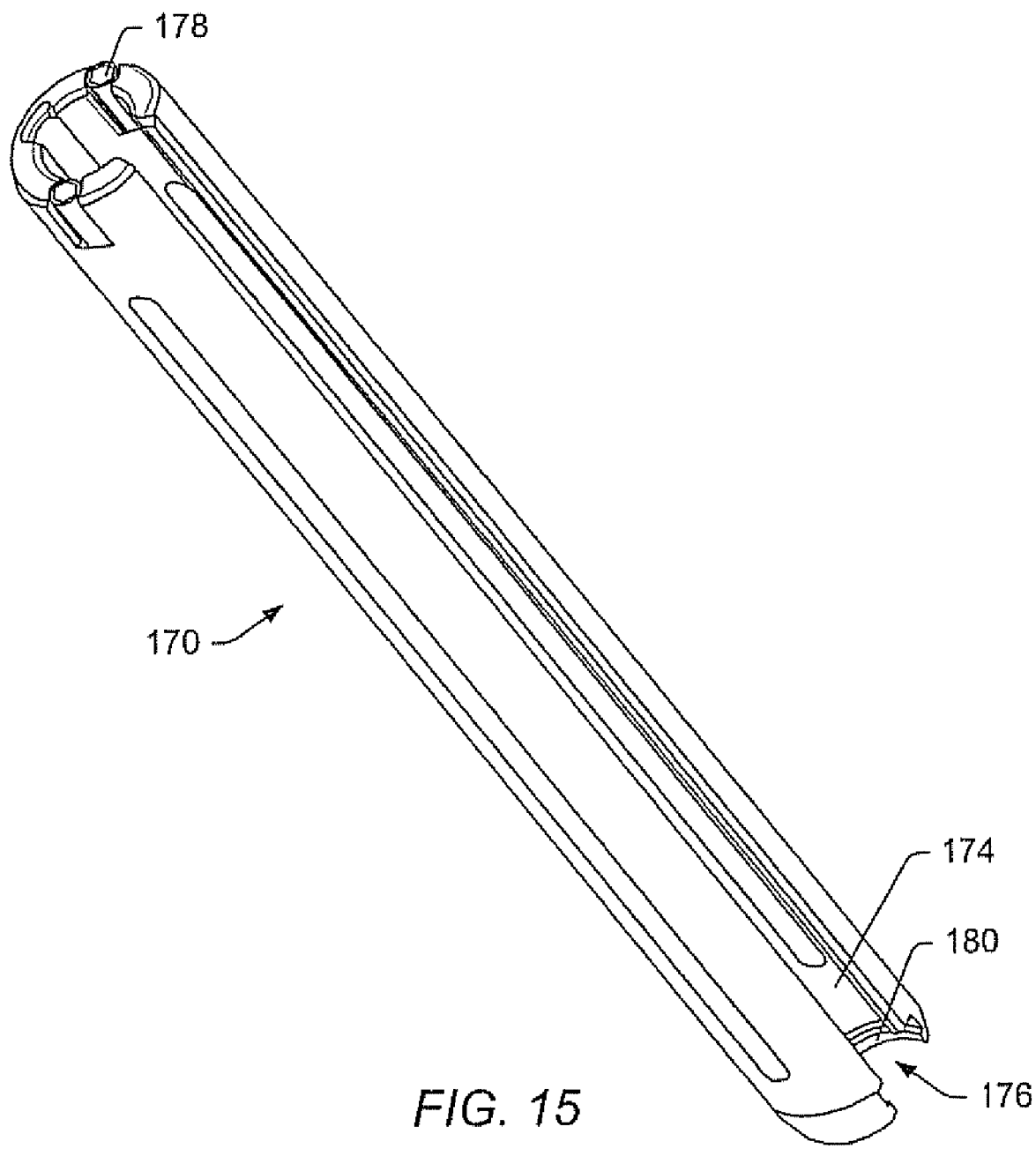
FIG. 15 depicts a perspective view of an embodiment of a single-channel extender.

FIG. 15 depicts an embodiment of extender 170. Extender 170 may be a single-channel extender for use in single-level or multi-level spinal stabilization procedures. Extender 170 may be used at the outermost vertebrae to be stabilized during installation of a multi-level vertebral stabilization system. Extender 170 may be coupled to a collar of a bone fastener assembly with movable members 178 and/or flange 180. Instruments may be inserted through passage 176 of extender 170 to access an anchored bone fastener assembly coupled to the extender. An instrument may be moved through channel 174 toward an adjacent vertebra to form a tissue plane in soft tissue between extender 170 and the adjacent vertebra.

An extender may be coupled to a collar of a bone fastener assembly in various ways. When an extender is coupled to a collar, rotation and translation of the extender relative to the collar may be inhibited. A system used to couple an extender and collar should be simple inexpensive to implement, and should not significantly weaken the mechanical strength of the collar and/or the extender. Extenders may be coupled to collars using various coupling systems including, but not limited to, flanges, threaded connections, interlocking connections (e.g., ratcheting connection systems), and/or interference fits.

Extenders may be of various lengths. Extenders of different lengths may be used in the same surgical procedure. An extender length used in a spinal stabilization procedure may be determined by a patient's anatomy. Extenders may be just short enough to allow manipulation by a medical practitioner above an incision in a patient. A multi-channel extender may be longer than a single-channel extender.

Figure 16:
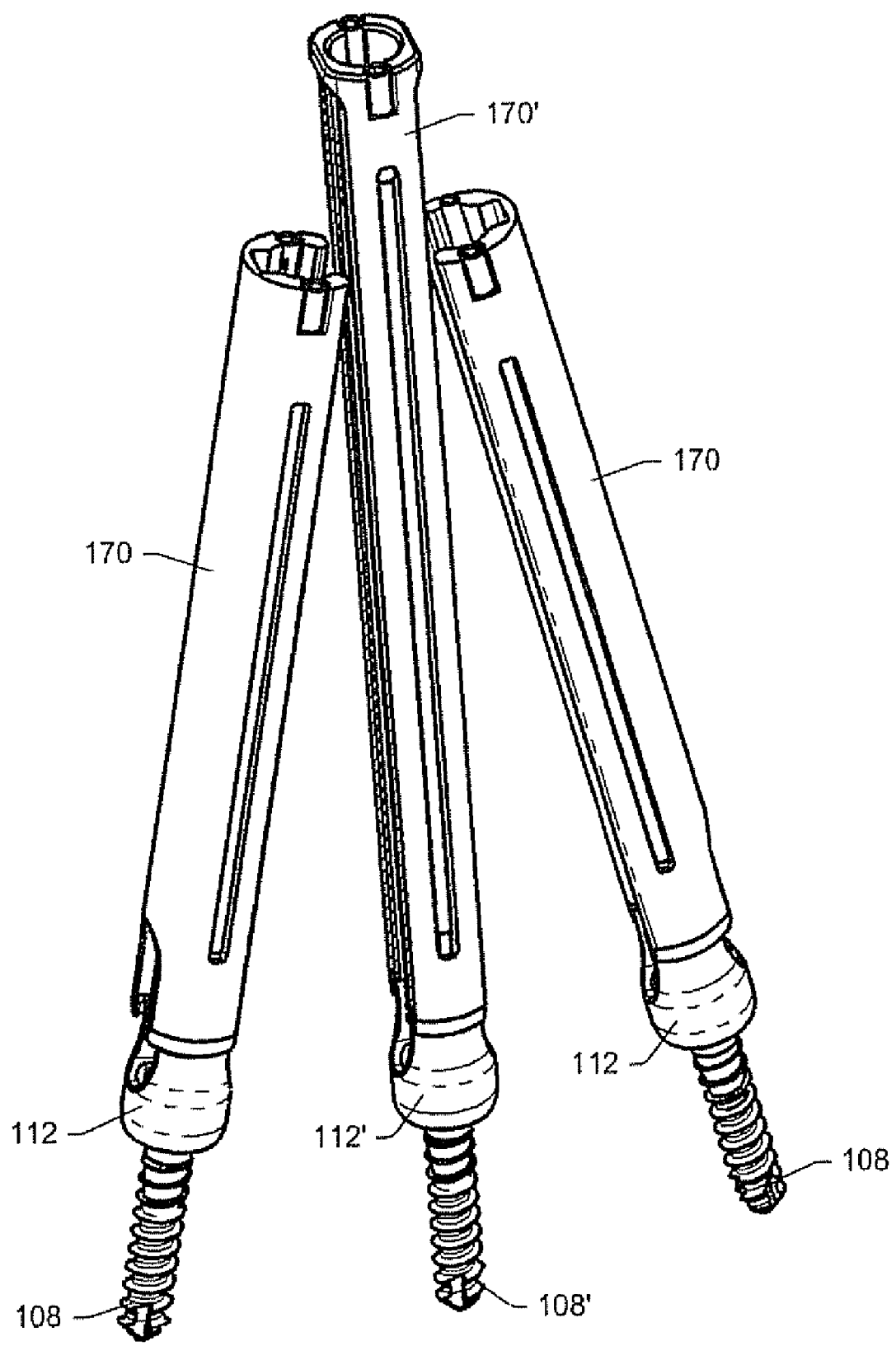
FIG. 16 depicts a perspective view of an embodiment of extenders coupled to bone fastener assemblies.

When bone fasteners of polyaxial bone fastener assemblies are positioned in vertebral bone, extenders coupled to collars of the bone fastener assemblies may be moved in desired positions. During surgery, an extender in a patient may be oriented towards an adjacent vertebra that is to be stabilized to reduce the required incision size. In some embodiments, channels of the extenders may be aligned so that an elongated member may be positioned in collars of the bone fastener assemblies. FIG. 16 depicts an orientation of the extenders. Extenders 170, 170' may couple to collars 112, 112'. Bone fasteners 108, 108' may be inserted into vertebrae. Single-channel extenders 170 may be coupled to collars 112 before insertion of bone fasteners 108 into two outer pedicles to be stabilized. Multi-channel extender 170' may be coupled to collar 112' before insertion of bone fastener 108' into a central pedicle of the three adjacent pedicles. Single-channel extenders 170 may be angled towards multi-channel extender 170'. Channels of the extenders may be aligned so that an elongated member may be moved down the extenders and into collars of the bone fastener assemblies.

After a bone fastener assembly is coupled to an extender, a driver may be coupled to a bone fastener of the bone fastener assembly. The driver may be used to insert the bone fastener into vertebral bone.

After bone fastener assemblies are installed and an elongated member is placed in the bone fastener assemblies, closure members may be secured to the bone fastener assemblies. When a closure member is threaded on a bone fastener assembly, a counter torque wrench may be used to inhibit the application of torque to the spine of the patient. A counter torque wrench may hold an extender that is coupled to a collar as the tool portion of a closure member is sheared off. In certain embodiments, about 90 in-lbs of torque may be required to shear off the tool portion of a closure member.

Figure 18:
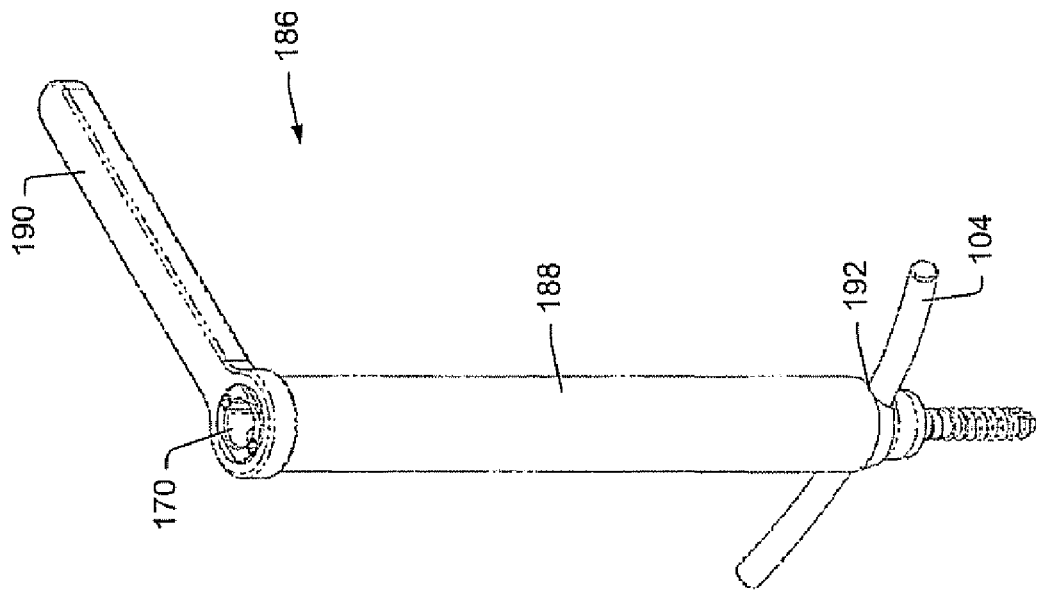
FIG. 18 depicts a schematic view of the sleeve shown in FIG. 17 coupled to an elongated member.
Figure 17:
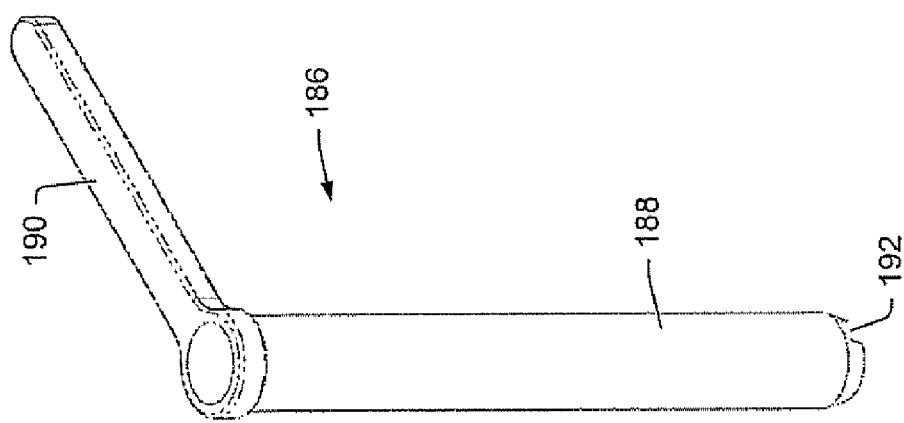
FIG. 17 depicts an embodiment of a sleeve that functions as a counter torque wrench.

In some embodiments, a counter torque wrench may inhibit application of torque to a patient during tightening of a closure member and/or during shearing of a tool portion of the closure member by applying a force to an elongated member to counter force applied to a bone fastener assembly by rotation of the closure member. The counter torque wrench may be a sleeve. FIG. 17 depicts an embodiment of a counter torque wrench that is a sleeve that couples to an elongated member. Sleeve 186 may include hollow shaft 188 and handle 190. Groove 192 may be located at a distal end of hollow shaft 188. FIG. 18 depicts sleeve 186 fitted over a multi-channel extender. In an embodiment, hollow shaft 188 may be inserted through an opening in the body over extender 170 and advanced toward the spine until elongated member 104 is seated in groove 192. Sleeve 186 may engage the spinal stabilization system. Force may be applied to sleeve 186 in a direction opposite to rotational force applied to a driver used to tighten and/or shear off a tool portion of a closure member. During a minimally invasive spinal stabilization procedure, sleeve 186 may be used with various types of extenders, including single-channel extenders and multi-channel extenders.

Figure 19:
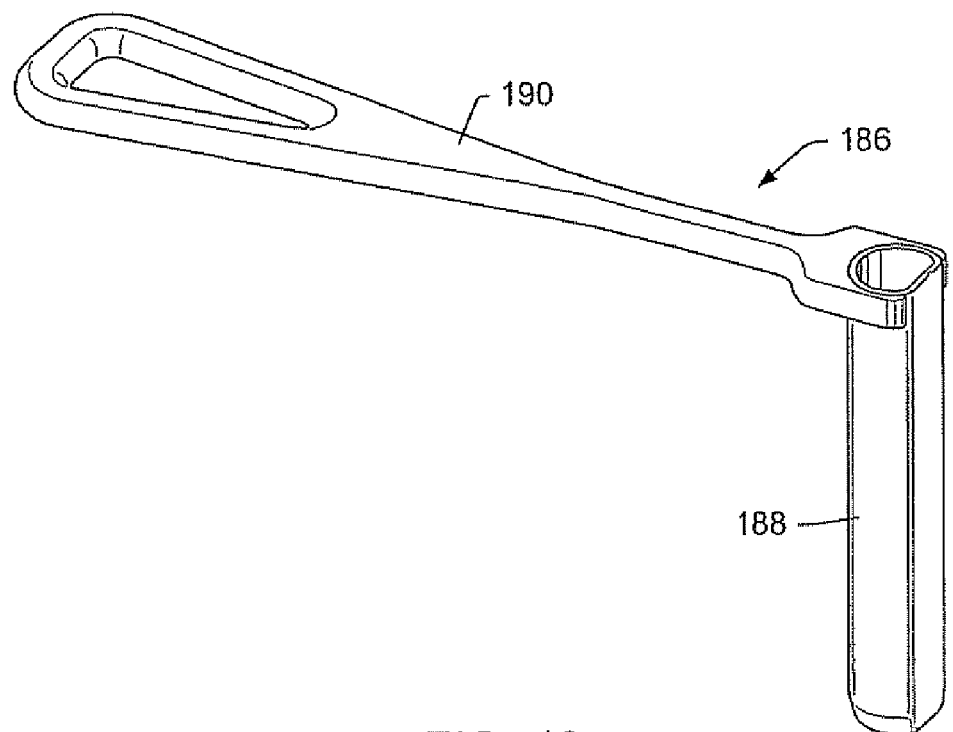
FIG. 19 depicts a perspective view of an embodiment of a sleeve.
Figure 20:
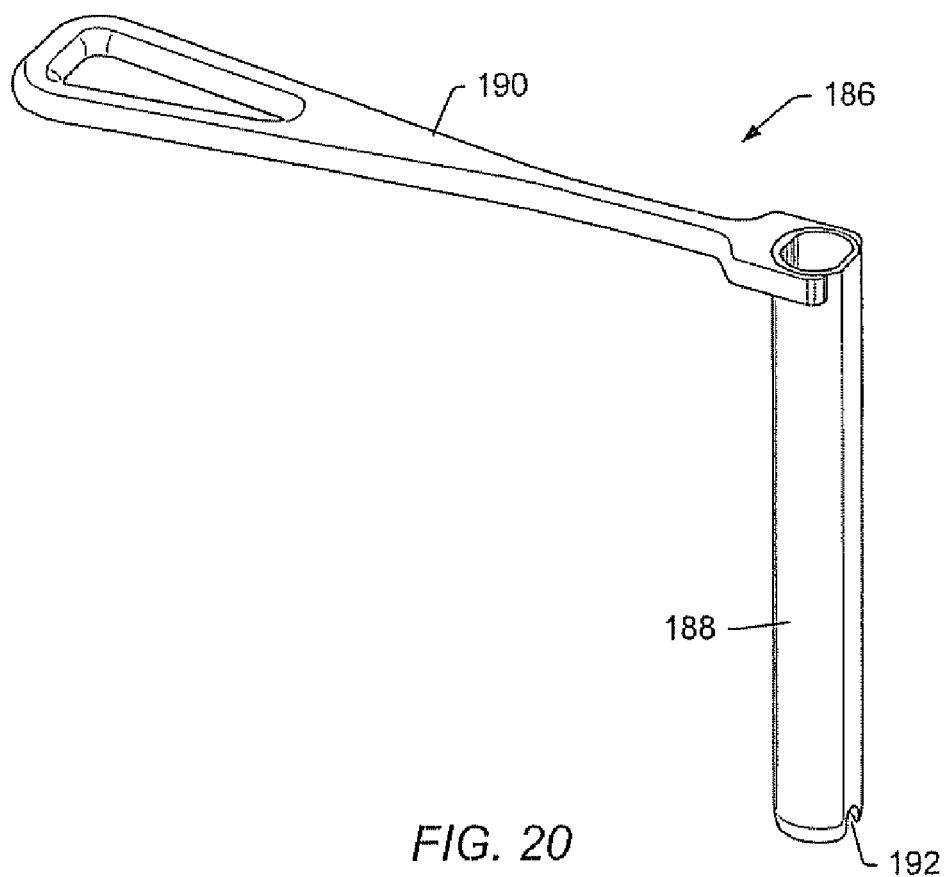
FIG. 20 depicts a perspective view of an embodiment of a sleeve.

In some embodiments, a shape of a hollow shaft of a sleeve may be configured to engage walls of an extender. The sleeve may include one or more flat portions. When a sleeve that is configured to engage a wall of an extender is placed over the extender, a rotational force applied to the sleeve may be transferred to the extender. The force applied to the extender may counter torque applied to a closure member. FIG. 19 depicts an embodiment of sleeve 186 configured to engage a single-channel extender. FIG. 20 depicts an embodiment of sleeve 186 configured to engage a multi-channel extender. Sleeves included in an instrument set may include indicia and/or color-coding to indicate the type of extender the sleeves are to be used with. As depicted in FIG. 20, some sleeve embodiments may include groove 192 configured to engage an elongated member of a stabilization system. As depicted in FIG. 19, some sleeve embodiments may not include a groove.

A hollow shaft of a sleeve may have a length that is less than a length of an extender that the sleeve is to be used with. For example, a length of a hollow shaft of a sleeve may be chosen such that a proximal portion of the extender protrudes from the proximal opening of the sleeve after positioning of the sleeve over the extender and against an elongated member during a spinal stabilization procedure. FIG. 19 depicts an embodiment of sleeve 186 with relatively short hollow shaft 188. FIG. 20 depicts an embodiment of sleeve 186 with relatively long hollow shaft 188.

Handle 190 of sleeve 186 may be of various shapes or designs. In some embodiments, a shape of handle 190 may facilitate gripping of sleeve 186. Handle 190 may include a cut-out portion to facilitate gripping and/or to reduce the weight of the sleeve. In certain embodiments, a shape of handle 190 may be tapered toward hollow shaft 188, as depicted in FIGS. 19 and 20, to reduce interference and/or increase visibility of a surgical site.

Figure 21:
FIG. 21 depicts an embodiment of an elongated member.
Figure 22:
FIG. 22 depicts an embodiment of an elongated member.
Figure 23:
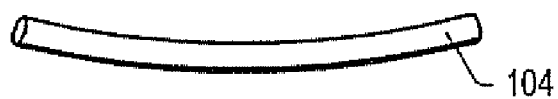
FIG. 23 depicts an embodiment of an elongated member.
Figure 24:
FIG. 24 depicts an embodiment of an elongated member.

An elongated member may be used to provide a desired shape to the spine of patient. Elongated members may have shapes including, but not limited to, straight, bent, curved, s-shaped, and z-shaped. FIG. 21 depicts an embodiment of S-shaped elongated member 104. FIG. 22 depicts an embodiment of angled elongated member 104. FIG. 23 depicts an embodiment of bent elongated member 104. FIG. 24 depicts an embodiment of straight elongated member 104. An instrumentation kit for a spinal stabilization system may include straight rods and/or pre-shaped rods. Straight rods and/or pre-shaped rods may be contoured to accommodate patient anatomy if needed during the surgical procedure.

In some embodiments, reducing one or more vertebral bodies to the shape of an elongated member (e.g., a contoured elongated member) may be indicated. Reduction of a vertebral body during a spinal stabilization procedure may include forcing the vertebral body into a position determined by the contour of the elongated member used in the spinal stabilization system.

During a spinal stabilization procedure, a first portion of an elongated member may be seated in a collar of a first bone fastener assembly that is coupled to a first vertebra. A closure member may be coupled to the collar and the elongated member to seat the elongated member fully in the collar and to fix the position of the elongated member relative to the first bone fastener assembly. A second portion of the elongated member may be positioned adjacent to a collar of a second bone fastener assembly that is coupled to a second vertebra. The position of the second vertebra and/or the shape of the elongated member may inhibit the second portion of the elongated member from being fully seated in the collar of the second bone fastener assembly. A reducer may be coupled to the elongated-member and to the collar of the second bone fastener assembly. The reducer may be used to fully seat the second portion of the elongated member in the collar of the second bone fastener assembly. While the reducer holds the second portion of the elongated member seated in the collar of the second bone fastener assembly, a driver may be used to secure a closure member to the collar to fix the position of the elongated member relative to the collar. Radiological imaging may be used to determine when the reducer has fully seated the second portion of the elongated member in the collar of the second bone fastener assembly.

Reducers may be used during a minimally invasive surgical procedure of during procedures where access to an elongated member and working room are restricted. During a minimally invasive procedure or a procedure with limited access and/or limited working room, a reducer may be used to pull an extender coupled to a bone fastener assembly of a spinal stabilization system upward (e.g., away from the spine) to seat the elongated member in a collar of the bone fastener assembly. Movement of a reducer may be achieved by, but is not limited to being achieved by, use of threading, cam action, linkage arms, or a combination thereof.

Figure 25:
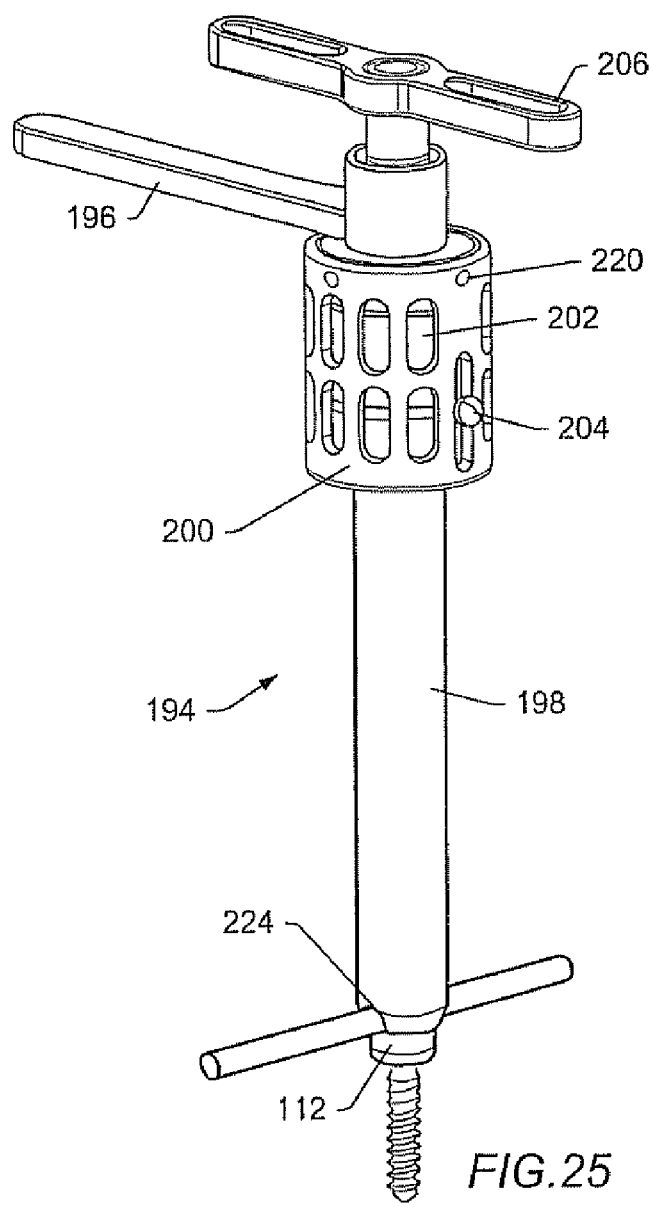
FIG. 25 depicts a perspective view of an embodiment of a reducer coupled to an elongated member.
Figure 26:
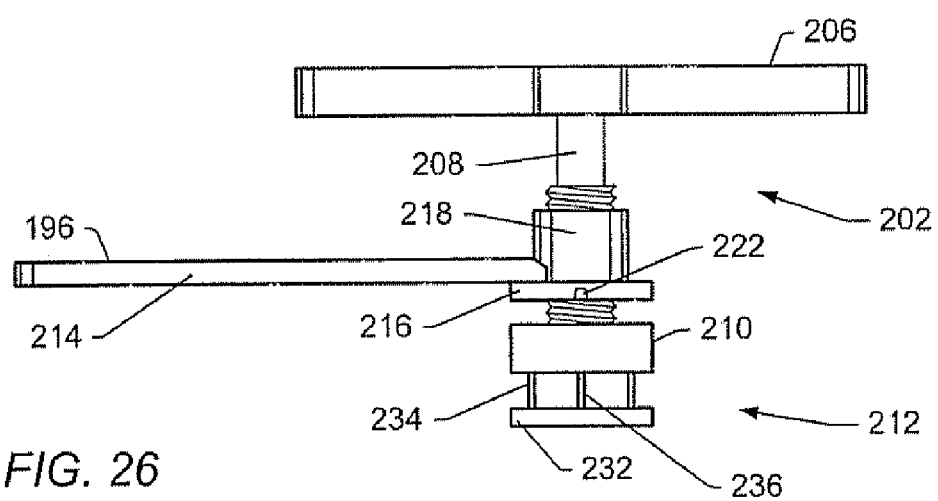
FIG. 26 depicts a front view of an embodiment of a movement mechanism and handle of the reducer depicted in FIG. 25.

FIG. 25 depicts an embodiment of reducer 194 for reduction of a vertebral body coupled to a spinal stabilization system. Reducer 194 may include handle 196, hollow shaft 198, cage 200, movement assembly 202 and grip 204 of a release mechanism. Hollow shaft 198 may be welded or otherwise fixed to cage 200. FIG. 26 depicts a front view representation of an embodiment of movement assembly 202 and handle 196. Movement assembly 202 may include rotator 206, threaded shaft 208, ring 210, and release mechanism 212. Handle 196 may include shank 214, base 216 and threaded collar 218. Shank 214 may be welded or otherwise coupled to base 216 and threaded collar 218. Threaded collar 218 may be threaded on threaded shaft 208 before ring 210 is welded or otherwise fixed to the threaded shaft.

As depicted in FIG. 25, ring 210 and release mechanism 212 may be placed in cage 200. An outer diameter of ring 210 and an outer diameter of release mechanism 212 may be slightly smaller than an inner diameter of cage 200. Stops 220 may be press fit, threaded or otherwise positioned in cage 200. An upper surface of ring 210 may contact stops 220 to inhibit separation of movement assembly 202 from cage 200.

Base 216 of handle 196 may include four or more slots 222. Slots 222 may engage stops 220 in cage 200. When slots 222 engage stops 220, rotation of shank 214 rotates cage 200 and hollow shaft 198. Orientation of handle 196 relative to groove 224 may be changed when ring 210 is positioned towards a bottom portion of cage 200. When ring 210 is positioned towards the bottom of cage 200, handle 196 may be lifted to remove base 216 from stops 220. Handle 196 may be rotated, and then lowered so that stops 220 engage slots 222 in base 216. Groove 224 may complement elongated member 104 so that counter torque may be applied to torque applied to collar 112 when a driver is used to secure a closure member to the collar.

A position of ring 210 relative to handle 196 may be changed by turning rotator 206 of movement assembly 202. In some embodiments, clockwise rotation of rotator 206 may draw ring 210 towards handle 196, and counterclockwise rotation of the rotator may move the ring away from the handle.

Figure 27:
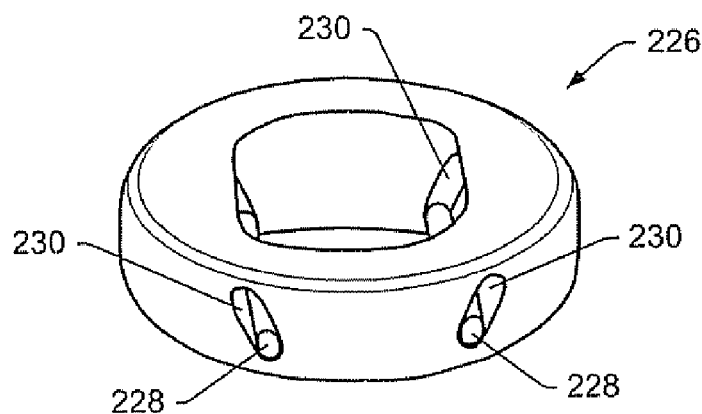
FIG. 27 depicts a perspective view of an internal ring of a reducer embodiment.

Ring 210 may include an internal ring. FIG. 27 shows a perspective view of an embodiment of internal ring 226. Internal ring may include a passage sized to allow an extender to pass through the ring. Internal ring 226 may include a pair of movable pins 228 seated in angled slots 230. When the hollow shaft of a reducer is placed over an extender and moved towards an elongated member, a top of the extender may contact movable pins 228 and push the movable pins upwards in angled slots 230. After the top of the extender passes by movable pins 228, the movable pins fall hack to the bottom of angled slots 230. If ring 210 moves upwards in cage 200, movable pins 228 engage a flange of the extender to translate the extender upward along with the ring.

An embodiment of a release mechanism is depicted in FIG. 26. Release mechanism 212 may be used to release an extender held by movable pins of ring 210. Release mechanism 212 may include platform 232, holders 234, pin engagers 236 and grip 204. Holders 234 may be positioned through platform 232. Holders 234 may be fixed to ring 210. Pin engagers 236 may be fixed to platform 232. Pin engagers 236 may slide in ring 210. Ends of pin engagers 236 are able to contact the movable pins in angled slots in ring 210. When grip 204 is grasped and moved towards ring 210 to move platform 232 towards the ring, the ends of pin engagers 236 contact the movable pins and move the movable pins in the angled slots in ring 210 so that the pins do not engage a flange of the extender. Moving the movable pins so that the movable pins do not engage the flange of the extender allows a user to grasp handle 196 and remove the reducer from the extender.

To use the reducer depicted in FIG. 25, rotator 206 may be turned to move ring 210 towards a bottom of cage 200. Hollow shaft 198 may be placed over an extender that is coupled to collar 112 of a bone fastener assembly. Hollow shaft 198 may be moved downwards until an end of the hollow shaft contacts elongated member 104 positioned in or above collar 112. Handle 196 may be rotated to position elongated member 104 in groove 224 of reducer 194. If desired, an orientation of handle 196 relative to elongated member 104 may be adjusted.

Rotator 206 may be rotated to move ring 210 towards handle 196. As ring 210 moves towards handle 196, movable pins in the ring engage a flange of the extender and move the extender towards the handle, seating elongated member 104 in collar 112. When elongated member 104 is fully seated in collar 112, a closure member coupled to a driver may be introduced through reducer 194 to the collar. The driver may be used to secure the closure member to collar 112. Reducer 194 may be used to provide counter torque to the force applied by the closure member to the collar.

Figure 28:
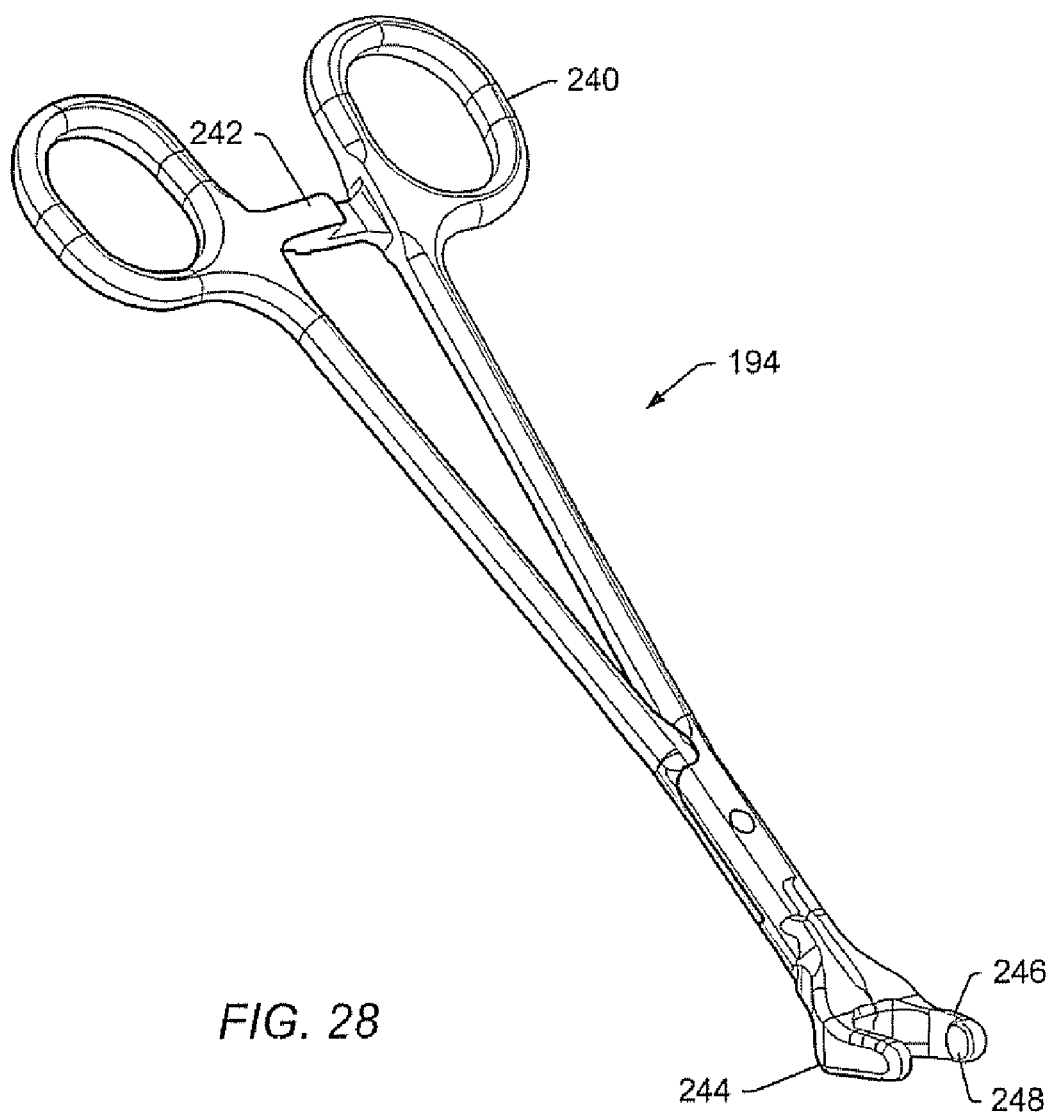
FIG. 28 depicts a perspective view of an embodiment of a reducer.

In some embodiments, a reducer may be used with one or more other instruments to achieve reduction of a vertebral body coupled to a spinal stabilization system. FIG. 28 depicts an embodiment of reducer 194 that may be used in combination with extender 170 and sleeve 186 depicted in FIG. 29. The reducer may be used to seat elongated member 104 in collar 112 of bone fastener assembly 102 when the bone fastener assembly is coupled to a vertebra. The reducer may be a forceps-type instrument designed to couple to recesses 238 in extender 170 and pull the extender upward while pushing elongated member 104 into collar 112.

As shown in FIG. 28, reducer 194 may include grips 240, locking mechanism 242, base 244, arms 246, and bosses 248. Movement of grips 240 away from each other may separate (e.g., open or increase a distance between) arms 246 of reducer 194. When arms 246 are separated, bosses 248 may be positioned adjacent to recesses of an extender. Grips 240 may be moved towards each other to position bosses 248 in the recesses of the extender. Bosses 248 may complement recesses in the extender so that reducer 194 may be rotated about the extender. In some embodiments, the reducer may include recesses, and the extender may include protrusions that fit within the recesses of the reducer during use. Locking mechanism 242 may fix the position of arms 246 relative to each other to inhibit separation of the arms when bosses 248 are positioned in recesses of the extender. In some embodiments, locking mechanism 242 may be interlocking teeth that form a ratchet system. Base 244 may be between bosses 248 and grips 240. Base 244 may function as a fulcrum during use. Bosses 248 may be offset from the same plane as grips 240. Reducer 194 may have a long length between base 244 and grips 240. The length of reducer 194 from base 244 to grips 240 may function as a lever arm during use.

During use, base 244 of reducer 194 may be placed on the handle of a sleeve. Grips 240 may be rotated towards the handle to move the extender upwards relative to the sleeve. Base 244 may function as a fulcrum of a lever system that moves the extender upwards relative to the sleeve. Moving the extender upwards relative to the sleeve may seat an elongated member in a collar that is coupled to the extender. When the elongated member is seated in the collar, a closure member coupled to a driver may be inserted through the extender to the collar. The closure member may be coupled to the collar. Counter torque to the force applied to the collar by the closure member may be applied to the sleeve.

Bone fastener assemblies that are coupled to extenders may be positioned in pedicles of vertebrae that are to be stabilized. An elongated member may be cut to length and contoured as desired. A medical practitioner may use experience and judgment to determine curvature of the elongated member for a patient. Determination of a desired curvature for the elongated member may be facilitated using radiological images of the patient. In some embodiments, a curvature of the elongated member may be chosen such that, when the elongated member is secured to the collars of the bone fastener assemblies, extenders coupled to the bone fastener assemblies cross at a surface of the skin. Crossing of the extenders at a surface of the skin allows the medical practitioner to minimize trauma to the patient. The elongated member may be bent or shaped with a tool (e.g., a rod bender) to allow insertion of the elongated member through channels of extenders with various spatial locations and/or various angular orientations.

Prior to insertion of the elongated member, a tissue wedge or targeting needle may be used to wand between the bone fasteners to ensure a clean tissue plane has been formed between the bone fasteners. An end of the elongated member may be inserted at an angle or substantially longitudinally in a passage and/or channel of an extender coupled to a bone fastener assembly. Inserting the elongated member at an angle or substantially longitudinally allows the length of the incision and/or the area of the tissue plane to remain advantageously small. In some embodiments, extenders coupled to anchored bone fastener assemblies may remain essentially unconstrained relative to each other during insertion of the elongated member. In certain embodiments, angular orientation of the collars may determine a trajectory of the elongated member down the extenders and into collars of the bone fastener assemblies. Inserting the elongated member down two or more extenders and through an open path (i.e., the tissue plane) may allow a medical practitioner to avoid surgical difficulties associated with anatomical abnormalities and/or misalignment of system components (e.g., in multi-level stabilization procedures). A positioning tool may be used to guide the elongated member down the extenders into slots in the collars.

During some spinal procedures, the elongated member may not initially seat in collars of the bone fastener assemblies. During such procedures, a reducer may be used to seat the elongated member in the collars of the bone fastener assemblies.

Reducer 194, depicted in FIG. 28, may be used in combination with a sleeve to forcefully reduce the difference in anterior-posterior position of one vertebral body with respect to one or more adjacent vertebral bodies coupled to a spinal stabilization system. In some cases, reduction may be performed to connect a deformity in a patient's spine. Reducer 194 may be used to achieve reduction across one or more vertebral levels at a time. For a multi-level spinal stabilization system, reduction may facilitate seating of an elongated member in a collar of the spinal stabilization system. Use of a reducer with a spinal stabilization system may allow a final position of a spine to be manipulated according to the contour of the elongated member.

Figure 30:
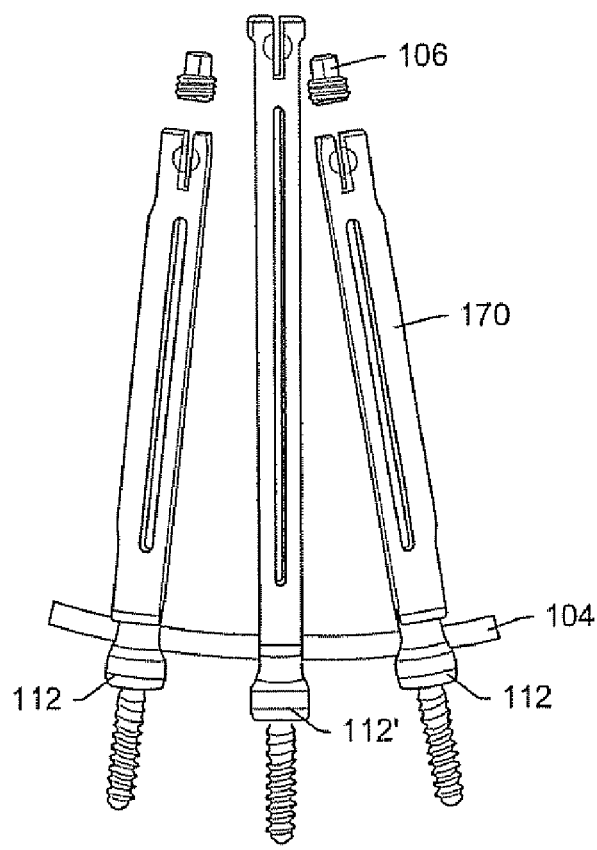
FIG. 30 depicts an embodiment of a spinal stabilization system before reduction.
Figure 31:
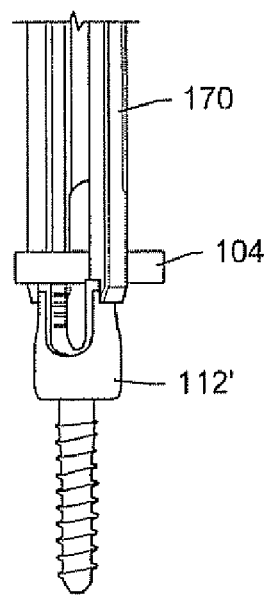
FIG. 31 depicts an embodiment of an unseated elongated member before reduction.

Before reduction is initiated, elongated member 104 may be positioned in collars 112 coupled to extenders 170 as depicted in FIG. 30. Closure members 106 may be positioned in one or more collars 112 such that elongated member 104 is at least loosely positioned in one or more of the collars. Elongated member 104 may be fully seated in collars 112. Elongated member 104 may not be fully seated in collar 112'. FIG. 31 depicts an enlarged perspective view of elongated member 104 proximate collar 112'.

Figure 29:
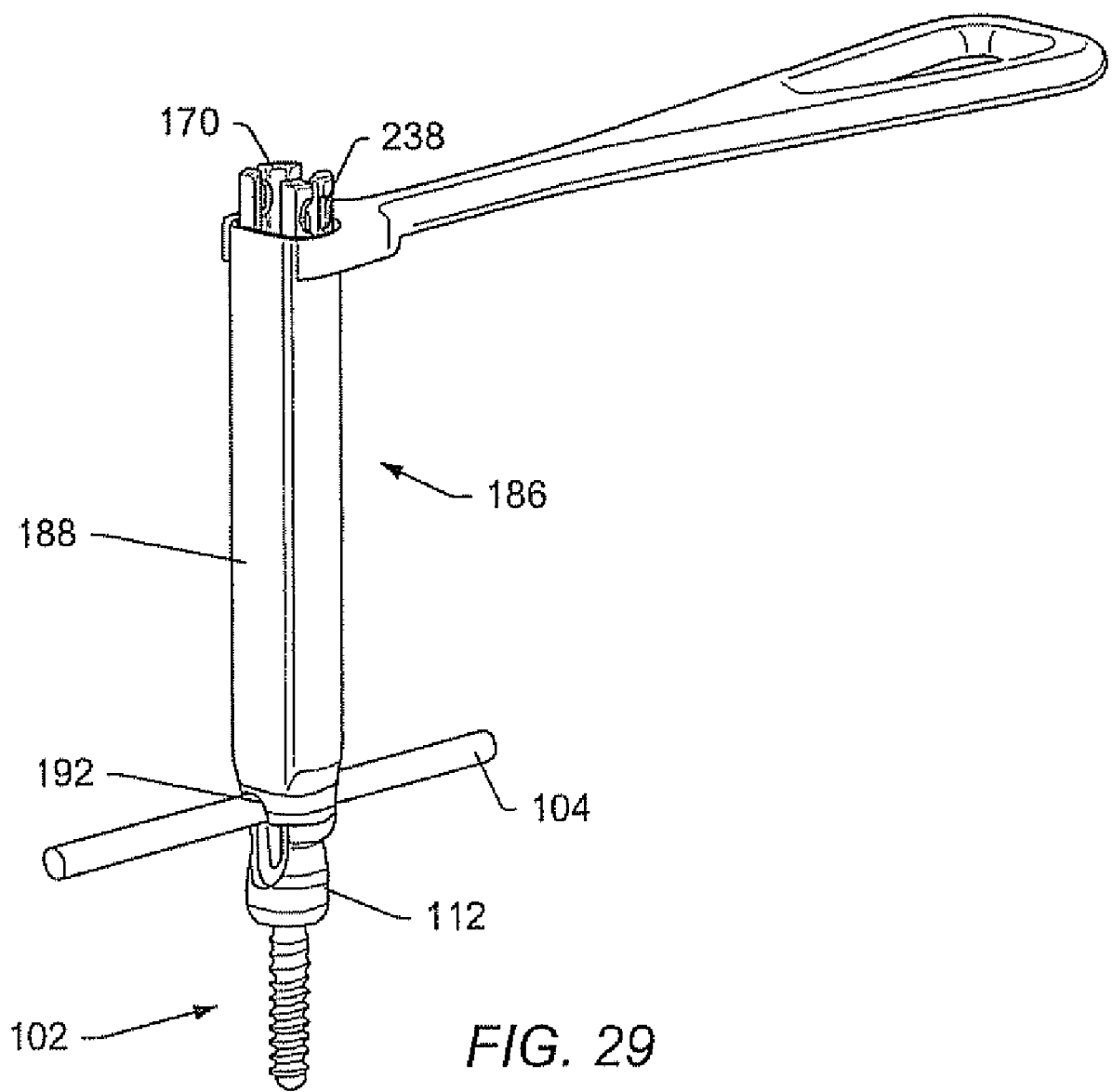
FIG. 29 depicts a perspective view of an embodiment of a sleeve positioned over an extender coupled to a spinal stabilization system that may be used with the reducer depicted in FIG. 28.

Sleeve 186 may be positioned over extender 170, engaging elongated member 104. In groove 192, as depicted in FIG. 29. In a multi-level spinal stabilization system, elongated member 104 may be fixed in place at one or more positions (e.g., secured in one or more of the outer collars with a closure member). A length of hollow shaft 188 of sleeve 186 may be chosen such that a proximal end of extender 170 protrudes from the proximal opening of the sleeve. In some embodiments, an instrumentation kit may provide sleeves 186 and extenders 170 that are sized to be used together such that recesses 238 in a proximal end of extender 170 are exposed above sleeve 186 during use. In certain embodiments, recesses 238 in extender 170 may be complementary to bosses 248 of reducer 194 depicted in FIG. 28.

Figure 32:
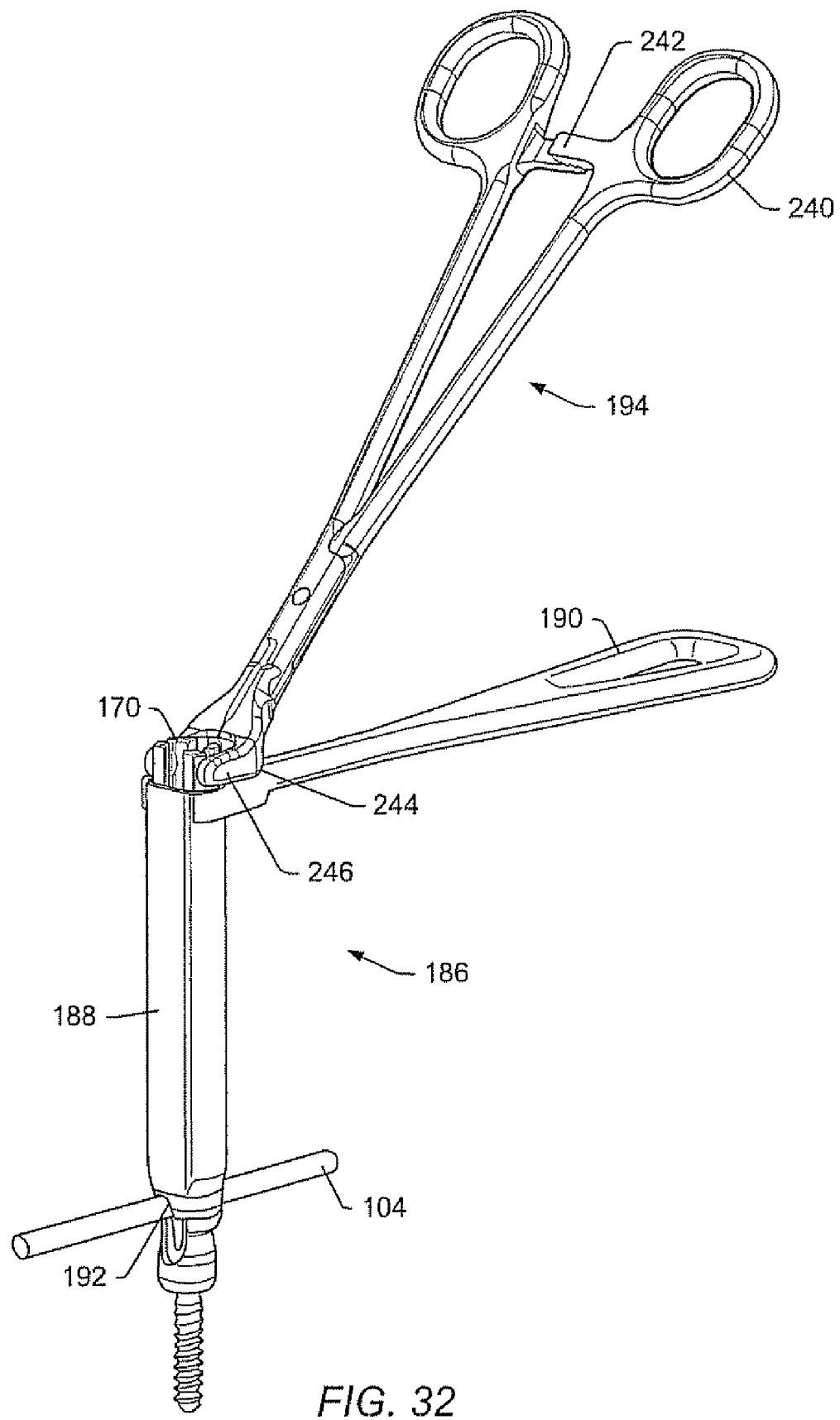
FIG. 32 depicts an embodiment of a reducer coupled to an extender before reduction.

FIG. 32 depicts reducer 194 coupled to extender 170 above a proximal opening of sleeve 186. To couple reducer 194 to extender, grips 240 may be spread apart to open arms 246 of the reducer. The bosses on arms 246 may be positioned proximate the recesses of extender 170. Grips 240 may be moved toward each other until the bosses of reducer 194 engage the recesses in extender 170. When the bosses engage the recesses, teeth of the locking mechanism 242 of reducer 194 may be engaged to inhibit undesired separation of arms 246 of the reducer. When the bosses engage the recesses, the base of reducer 194 may be positioned on handle 190 of sleeve 186.

Figure 33:
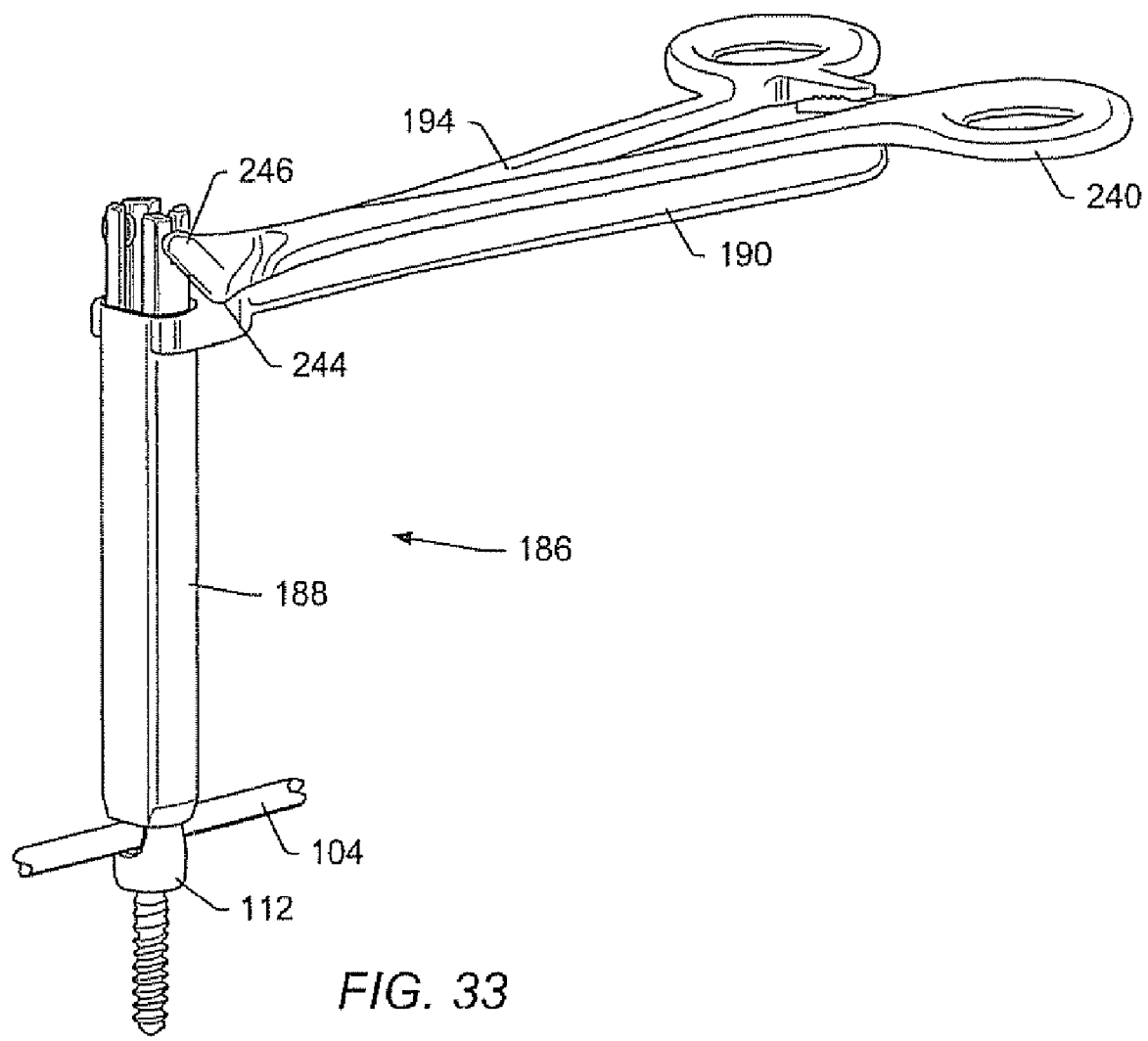
FIG. 33 depicts an embodiment of a reducer coupled to an extender after reduction.

With reducer 194 coupled to extender 170 and aligned with handle 190 of sleeve 186, reduction may be achieved by rotating grips 240 about base 244 downward toward the handle. As grips 240 of reducer 194 are forced toward handle 190 of sleeve 186, extender 170 may translate upward through hollow shaft 188 of the sleeve. Translation of extender 170 upward through hollow shaft 188 may effectively pull the vertebral body to which the extender is coupled toward elongated member 104, seating the elongated member in collar 112. Grips 240 of reducer 194 may be rotated towards handle 190 of sleeve 186 until elongated member 104 is seated in collar 112, as depicted in FIG. 33. In some embodiments, reducer 194 may move extender 170 a vertical distance of from about 0.1 mm to about 40 mm. For example, reducer 194 may move extender 170 a vertical distance of about 10 mm during use. For example, vertebral reduction of about 6 mm to about 12 mm may be achieved. In some embodiments, a first vertebral body may be translated a distance of at least 5 mm relative to a second vertebral body.

With elongated member 104 fully seated in collar 112, reduction may be maintained by maintaining a force on reducer 194 that drives grips 240 towards handle 190 of sleeve 186. A closure member driver may be inserted in extender 170 to secure a closure member in collar 112. Securing a closure member in collar 112 may fasten elongated member 104 in place. In some embodiments, sleeve 186 may also be used as a counter torque wrench during tightening of the closure member to inhibit counteract force applied to collar by rotation of the closure member. Reducer 194 may be removed from extender 170. The reduction procedure may advantageously be performed by one person.

After an elongated member has been positioned and seated in collars as desired, closure members may be used to secure the elongated member to the collars. One or more counter torque wrenches (e.g., sleeves) may be used during shearing of the tool portions of the closure members.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A system for use in spine surgery, comprising:
a rod;
a first bone screw configured to be coupled to a first vertebra;
a first collar coupled to the first bone screw, said first collar comprising a first slot for seating the rod;
a first extender configured to be detachably coupled to the first collar;
a second bone screw configured to be coupled to a second vertebra;
a second collar coupled to the second bone screw, said second collar comprising a second slot for seating the rod;
a sleeve positioned over at least a portion of the first extender, wherein the sleeve includes a first end, a second end, and a length extending therebetween, wherein a first end of the sleeve is configured to engage and seat the rod in the first slot; and
a reducer configured to translate the first extender and the first collar relative to the sleeve; and
whereby when the first bone screw is coupled to the first vertebra, the second bone screw is coupled to the second vertebra, the first extender is detachably coupled to the first collar, and the rod is at least partially seated in the second slot, the reducer is configured to translate the first extender relative to the sleeve such that the first end of the sleeve engages the rod to facilitate seating the rod in the first slot; wherein the reducer comprises at least one boss configured to couple to a recess in the first extender, and wherein the reducer comprises a base configured to engage the sleeve; wherein the sleeve includes a handle and the reducer includes arms and grips, wherein the first extender and the first collar are translated relative to the sleeve by rotating the grips of the reducer about the base towards the handle of the sleeve.

2. The system of claim 1, further comprising a closure member configured to be coupled to the first collar when the reducer seats the rod in the first slot.

3. The system of claim 2, further comprising a driver configured to secure the closure member to the collar.

4. The system of claim 1, further comprising a second extender configured to be detachably coupled to the second collar.

5. The system of claim 1, wherein the reducer comprises:
a rotator, wherein turning the rotator in a first direction translates the first extender relative to the sleeve and seats the rod in the first collar.

6. A system for use in spine surgery, comprising:
a rod;
a first bone fastener configured to be coupled to a first vertebra;
a first collar coupled to the first bone fastener, said first collar comprising a first slot for seating the rod;
a first extender configured to detachably couple to the first collar;
a first sleeve configured to surround a portion of the first extender, the first sleeve including a first end configured to engage and seat the rod in the first slot;
a second bone fastener configured to be coupled to a second vertebra;
a second collar coupled to the second bone fastener, said second collar comprising a second slot for seating the rod;
a reducer configured to engage the first sleeve, said reducer configured to translate the first extender and the first collar relative to the second collar; and
whereby when the first bone fastener is coupled to the first vertebra, the second bone fastener is coupled to the second vertebra, the first extender is detachably coupled to the first collar, the reducer is engaged to the first sleeve, and the rod is at least partially seated in the second slot, rotation of the reducer relative to the first sleeve seats the rod in the first slot; wherein the reducer comprises bosses that are configured to engage recesses in the first extender, and wherein the reducer comprises a base configured to engage the sleeve; wherein the sleeve includes a handle and the reducer includes arms and grips, wherein the first extender and the first collar are translated relative to the sleeve by rotating the grips of the reducer about the base towards the handle of the sleeve.

7. The system of claim 6, further comprising a closure member configured to couple the first collar to secure the rod relative to the first collar.

8. The system of claim 6, further comprising a driver configured couple to a closure member, wherein the driver is configured to be positioned in the first extender when the reducer is in use to seat the rod in the first slot.

9. The system of claim 1, wherein the reducer is configured to engage the first extender adjacent to the second end of the sleeve.

10. The system of claim 1, wherein the reducer is a forceps-type instrument.

11. The system of claim 1, wherein the reducer includes a locking mechanism to fix the position of arms relative to each other.

12. The system of claim 6, wherein the reducer is configured to engage the first extender adjacent to the second end of the sleeve.

13. The system of claim 6, wherein the reducer is a forceps-type instrument.

14. The system of claim 6, wherein the reducer includes a locking mechanism to fix the position of arms relative to each other.

* * * * *

UNITED STATES PATENT AND TRADEMARK OFFICE
CERTIFICATE OF CORRECTION

PATENT NO. : 7,985,242 B2
APPLICATION NO. : 11/690698
DATED : July 26, 2011
INVENTOR(S) : Charlie Forton et al.

It is certified that error appears in the above-identified patent and that said Letters Patent is hereby corrected as shown below:

Column 8
Line 8, delete "reading", and insert therefor -- threading --.

Column 12
Line 11, delete "the", and insert therefor -- three --.

Column 14
Line 4, delete "of", and insert therefor -- or --.

Column 16
Line 65, delete "connect", and insert therefor -- correct --.

Signed and Sealed this
Thirtieth Day of August, 2011

David J. Kappos
*Director of the United States Patent and Trademark Office*